(12) United States Patent
Austad et al.

(10) Patent No.: US 8,716,479 B2
(45) Date of Patent: May 6, 2014

(54) METHODS FOR STEREOSELECTIVE REDUCTION

(75) Inventors: Brian C. Austad, Tewksbury, MA (US); Andre Lescarbeau, Somerville, MA (US); Lin-Chen Yu, Quincy, MA (US)

(73) Assignee: Infinity Pharmaceuticals, Inc., Cambridge, MA (US)

( * ) Notice: Subject to any disclaimer, the term of this patent is extended or adjusted under 35 U.S.C. 154(b) by 690 days.

(21) Appl. No.: 12/810,600

(22) PCT Filed: Dec. 24, 2008

(86) PCT No.: PCT/US2008/088302
§ 371 (c)(1),
(2), (4) Date: Sep. 15, 2010

(87) PCT Pub. No.: WO2009/086451
PCT Pub. Date: Jul. 9, 2009

(65) Prior Publication Data
US 2011/0009442 A1    Jan. 13, 2011

Related U.S. Application Data

(63) Continuation-in-part of application No. 11/965,688, filed on Dec. 27, 2007.

(60) Provisional application No. 61/017,162, filed on Dec. 27, 2007.

(51) Int. Cl.
*C07D 471/02* (2006.01)
*C07D 311/96* (2006.01)

(52) U.S. Cl.
USPC ............. 546/17; 546/115; 549/331; 549/345

(58) Field of Classification Search
USPC ................ 546/17, 115; 549/331, 345
See application file for complete search history.

(56) References Cited

U.S. PATENT DOCUMENTS

| | | |
|---|---|---|
| 6,291,516 B1 | 9/2001 | Dudek et al. |
| 6,432,970 B2 | 8/2002 | Beachy et al. |
| 6,686,388 B2 | 2/2004 | Dudek et al. |
| 6,867,216 B1 | 3/2005 | Beachy et al. |
| 7,098,196 B1 | 8/2006 | Beachy et al. |
| 7,230,004 B2 | 6/2007 | Adams et al. |
| 7,291,626 B1 | 11/2007 | Beachy et al. |
| 7,407,967 B2 | 8/2008 | Adams et al. |
| 7,476,661 B2 | 1/2009 | Beachy et al. |
| 7,605,167 B2 | 10/2009 | Tas et al. |
| 7,629,352 B2 | 12/2009 | Tas et al. |
| 7,648,994 B2 | 1/2010 | Castro et al. |
| 7,812,164 B2 | 10/2010 | Austad et al. |
| 7,867,492 B2 | 1/2011 | Beachy et al. |
| 7,875,628 B2 | 1/2011 | Adams et al. |
| 7,893,078 B2 | 2/2011 | Tas et al. |
| 7,964,590 B2 | 6/2011 | Castro et al. |
| 7,994,191 B2 | 8/2011 | Castro et al. |
| 8,017,648 B2 | 9/2011 | Castro et al. |
| 2003/0114393 A1 | 6/2003 | Liscovitch et al. |
| 2003/0220314 A1 | 11/2003 | Shackleton et al. |
| 2004/0127474 A1 | 7/2004 | Dudek et al. |
| 2006/0020020 A1 | 1/2006 | Dudek et al. |
| 2006/0142245 A1 | 6/2006 | Beachy et al. |
| 2007/0231828 A1 | 10/2007 | Beachy et al. |
| 2008/0019961 A1 | 1/2008 | Wicha et al. |
| 2008/0057071 A1 | 3/2008 | Watkins et al. |
| 2008/0058298 A1 | 3/2008 | Beachy et al. |
| 2008/0089915 A1 | 4/2008 | Tas et al. |
| 2008/0095761 A1 | 4/2008 | Beachy et al. |
| 2008/0118493 A1 | 5/2008 | Beachy et al. |
| 2008/0255059 A1 | 10/2008 | Beachy et al. |
| 2008/0287420 A1 | 11/2008 | Castro et al. |
| 2008/0293755 A1 | 11/2008 | Castro et al. |
| 2009/0012109 A1 | 1/2009 | Austad et al. |
| 2009/0216022 A1 | 8/2009 | Austad et al. |
| 2009/0286822 A1 | 11/2009 | Tas et al. |
| 2010/0003728 A1 | 1/2010 | Jayatilake et al. |
| 2010/0144775 A1 | 6/2010 | Castro et al. |
| 2010/0273818 A1 | 10/2010 | Beachy et al. |
| 2010/0286180 A1 | 11/2010 | Castro et al. |
| 2011/0104254 A1 | 5/2011 | Tas et al. |
| 2011/0135739 A1 | 6/2011 | Carter et al. |
| 2011/0166353 A1 | 7/2011 | Adams et al. |
| 2011/0230509 A1 | 9/2011 | Castro et al. |
| 2012/0015934 A1 | 1/2012 | Castro et al. |

FOREIGN PATENT DOCUMENTS

| | | |
|---|---|---|
| EP | 0434570 | 6/1991 |
| WO | WO94/20520 | 9/1994 |
| WO | WO2006/026430 | 3/2006 |
| WO | WO2008/083248 | 7/2008 |

(Continued)

OTHER PUBLICATIONS

Brown, D. et al. "Structure-activity relation of steroid teratogens. 1. Jervine ring system", J. Agric. Food. Chem., vol. 26, (1978), pp. 561-563.
Brown, D. et al., "Structure-activity relation of steroid teratogens. 2. N-Substituted jervines" , J. Agric. Food. Chem., vol. 26, (1978), pp. 564-566.
Djerassi, C. et al. "Selective Reduction of Steroids by Homogeneous Catalytic Hydrogenation", Journal of the American Chemical Society, vol. 88, No. 9, (1966), pp. 4537-4538.
Heretsch, P. et. al., "Cyclopamine and Hedgehog Signaling: Chemistry, Biology, Medical Perspectives" Angewandte Chemie, International Edition, vol. 49, No. 20, (2010), pp. 3418-3427.
Incardona, J.P. et al., "Cyclopamine Inhibition of Sonic Hedgehog Signal Transduction Is Not Mediated through Effects on Cholesterol Transport", Developmental Biology, (2000), pp. 440-452.

(Continued)

*Primary Examiner* — Andrew D Kosar
*Assistant Examiner* — Raymond Covington
(74) *Attorney, Agent, or Firm* — Fish & Richardson P.C.

(57) ABSTRACT

The invention is directed to a method to reduce a C—C double bond of an enone of a steroidal compound to produce a mixture of β ketone product and α ketone product, comprising treating a solution or suspension of the steroidal compound in a solvent with hydrogen gas in the presence of a catalyst and a substituted pyridine.

16 Claims, No Drawings

(56) References Cited

FOREIGN PATENT DOCUMENTS

| WO | WO2008/109184 | 9/2008 |
|---|---|---|
| WO | WO2008/109829 | 9/2008 |
| WO | WO2009/126840 | 10/2009 |
| WO | WO2010/000070 | 1/2010 |

OTHER PUBLICATIONS

Leontjev, A.E. et al., "Reduction of steroidal ketones with Amine-boranes", Russian Chemical Bulletin, vol. 53, No. 3, (2004), pp. 703-708.

Paryzek, Z. et al., "Ammonium Formate/Palladium on Carbon: A Versatile System for Catalytic Hydrogen Transfer Reductions of Carbon—Carbon Double Bonds", Synthesis, No. 13, (2003), pp. 2023-2026.

Ravasio, N. et al., "Selective Hydrogenations Promoted by Copper Catalysts. 1. Chemoselectivity, Regioselectivity, and Stereoselectivity in the Hydrogenation of 3-Substituted Steroids", Journal of Organic Chemistry, vol. 56, No. 13, (1991), pp. 4329-4333.

Reddy, G. Vidya Sagar et al., "A New Novel and Practical One Pot Methodology for Conversion of Alcohols to Amines", Synthetic Communications, vol. 30, No. 12, (2002), pp. 2233-2237.

Shner, V. F. et al., "The Stereospecificity of the Hydrogenation of 16-alpha-Methyl-3-oxo-delta-4-UnSaturated Compounds", Chemistry of Natural Compounds, vol. 6, No. 1, (1970), pp. 53-56.

Suggs, J. W., Facile Homogeneous Hydrogenations of Hindered Olefins With [Ir(cod)py(PCy3)]PF6, Tetrahedron Letters, vol. 22, (1981), pp. 303-306.

Tsuji, N. et al., "Highly Stereoselective Hydrogenation of 3-Oxo-4-ene and -1,4-diene Steroids to 5β Compounds with Palladium Catalyst", Journal of Organic Chemistry, vol. 45, (1980), pp. 2729-2731.

Zeng, C., "Neurosteroid Analogues. 10. The Effect of Methyl Group Substitution at the C-6 and C-7 Positions on the GABA Modulatory and Anesthetic Actions of (3α,5α) and (3α,5β)-3-Hydroxypregnan-20-one", Journal of Medicinal Chemistry, vol. 48, No. 8, (2005), pp. 3051-3059.

International Search Report and the Written Opinion of the International Searching Authority for counterpart Application No. PCT/US2008/88302 dated Mar. 25, 2009, (9 pages).

Natsuko Tsuji et al., "Highly Stereoselective Hydrogenation of 3-oxo-4-ene and -1, 4-diene Steroids to 5.beta.-Compounds with Palladium Catalyst," Journal of Organic Chemistry, 45(13):2729-2731 (1980).

Masamune Tadashi et al., "Synthesis and nuclear magnetic resonance spectra of 22, 27-imino-17, 23-epoxyjervane derivatives," Tetrahedron, 23(4):1591-1612 (1967).

METHODS FOR STEREOSELECTIVE REDUCTION

This application is the U.S. National Stage of PCT/US2008/088302, filed on Dec. 24, 2008, which is a continuation-in-part of U.S. patent application Ser. No. 11/965,688, filed Dec. 27, 2007, and which claims the benefit of U.S. Provisional Application No. 61/017,162, filed Dec. 27, 2007, each of these prior applications is incorporated by reference in its entirety.

BACKGROUND

Polycyclic compounds such as steroidal compounds have a wide variety of uses, for example, as pharmaceutical agents. In steroidal compounds that contain enone moieties, it is sometimes desirable to stereo selectively reduce the C—C double bond to preferentially produce either the β-reduced or the α-reduced compound. In either event, it is useful to reduce the C—C double bond stereoselectively in order to obviate complex chromatographic purifications.

SUMMARY

The invention relates to a method of reducing the C—C double bond of an enone of a steroidal compound to produce a mixture of β ketone product and α ketone product, by treating a solution or suspension of the steroidal compound in a solvent with hydrogen gas in the presence of a catalyst and a substituted pyridine. In some instances, an excess of the β ketone product is produced compared to the α ketone product. The invention also relates to compounds made by the described methods.

DETAILED DESCRIPTION

In one aspect, the invention relates to a method of reducing the C—C double bond of an enone of a steroidal compound to produce a mixture of β ketone product and α ketone product, the method comprising treating a solution or suspension of the steroidal compound in a solvent with hydrogen gas in the presence of a catalyst and a substituted pyridine. In some embodiments, an excess of the β ketone product is produced compared to the α ketone product. For example, the ratio of the β ketone product to the α ketone product can be at least about 2:1, about 3:1, about 5:1, about 10:1, about 20:1, about 25:1, about 30:1, about 40:1, about 50:1, about 60:1, about 70:1, about 80:1, about 90:1, about 95:1, or greater than about 99:1.

In some embodiments, the substituted pyridine is a 3-substituted pyridine. Examples of suitable 3-substituted pyridines include 3-picoline, 3-methoxypyridine, 3-ethylpyridine, 3-n-butylpyridine, 3-isobutylpyridine, 3-hydroxypyridine, 3-aminopyridine, and 3-dimethylaminopyridine. In other embodiments, the substituted pyridine is a 4-substituted pyridine (e.g., 4-picoline, 4-methoxypyridine, 4-aminopyridine, or 4-dimethylaminopyridine).

In some embodiments, the substituted pyridine is the reaction solvent. In other embodiments, the solvent is a solvent other than the substituted pyridine. Any solvent that does not interfere with the reduction reaction may be employed, including, for example, ethers (e.g., THF), chlorinated solvents (e.g., chloroform, dichloromethane) and aromatics (e.g., benzene, toluene). In addition, a mixture of one or more solvents may be used. When another solvent is used, the v/v percentage of substituted pyridine to the total volume can be about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99%.

Suitable hydrogenation catalysts include heterogeneous catalysts and homogeneous catalysts. Examples of homogeneous catalysts include, for example, metal catalysts based on nickel (e.g., Raney nickel, nickel boride), palladium (e.g., Pd/C), platinum (e.g., platinum oxide), rhodium, ruthenium, or zinc (e.g., zinc oxide). Examples of homogeneous catalysts include, for example, metal catalysts based on rhodium (e.g., Wilkinson's catalyst), ruthenium, palladium, platinum or cobalt. Any hydrogenation catalyst known in the art to reduce the double bond of an enone may be employed (see, e.g., March, *Advanced Organic Chemistry*). In some embodiments, the catalyst is a palladium-based catalyst, for example, palladium on carbon (e.g., 5% or 10% Pd/C), palladium on $Al_2O_3$, palladium hydroxide on carbon (Pearlman's catalyst), and palladium and platinum on carbon (e.g., 4% Pd/1% Pt on carbon). Suitable hydrogenation catalysts can be obtained from commercial sources (e.g., Johnson Matthey).

In some embodiments, the hydrogen is applied to the reaction at or near atmospheric pressure (i.e., at 1 atm.) for example, under balloon pressure. In other embodiments, the hydrogen is applied to the reaction at increased pressure (e.g., 1 to 5 atm. or greater), for example, using a Parr shaker or similar apparatus.

The method of the invention provides for stereoselective hydrogenation of an enone double bond present in a steroidal compound. Steroidal compounds generally contain a fused four-ring system core. For example, steroidal ring systems can include 6, 6, 6, 5 ring systems (e.g., cyclopenta[a]phenanthrene) or 6, 6, 5, 6, ring systems, wherein each ring is designated A, B, C, or D as shown below:

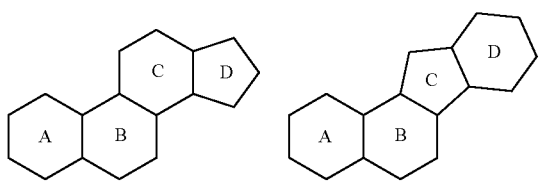

Steroidal compounds also include homo-analogs (i.e., wherein one or more rings contain additional carbons) and nor-analogs (i.e., wherein one or more rings contain one or more fewer carbons), and mixtures of both (i.e., wherein one or more rings contain additional carbons and one or more rings contain fewer carbons). One such example is the 6, 6, 5, 7 ring system:

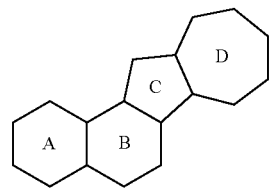

In addition, one or more additional rings may be fused or bonded to the steroidal core. Included within this group are steroidal alkaloids having the following general structures:

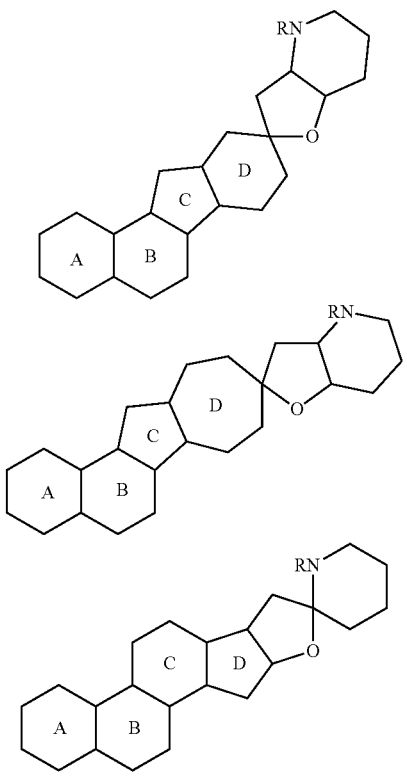

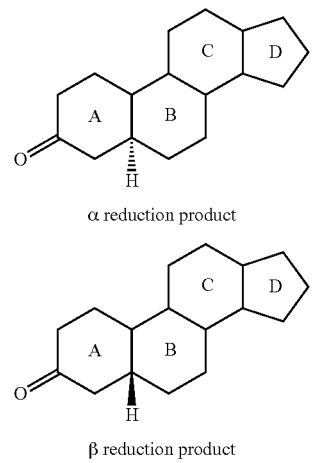

α reduction product

β reduction product

Steroidal compounds also include des-analogs, wherein one of the four fused rings is missing (e.g., a 6, 6, 5 ring system).

Generally, the enone that is reduced according to the present invention is present in the A ring of the steroidal compound. The ketone carbonyl may be bonded to any carbon of the A ring (as valency permits), and one or more double bonds may be present in the ring. For example, the enone may have any of the following configurations:

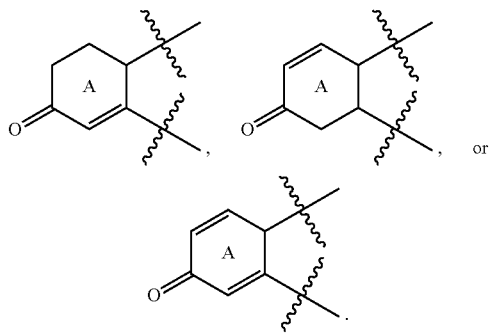

When the rings of a steroid are denoted with the A ring on the left (as shown herein), an atom or group attached to a ring is termed α if it lies below the plane of the paper and β if it lies above the plane of the paper:

Any of the carbons in the steroidal backbone may bear substituents. Exemplary substituents include hydrogen, optionally substituted alkyl, optionally substituted alkenyl, optionally substituted alkynyl, halogen, hydroxyl, optionally substituted alkoxyl, optionally substituted amino, optionally substituted amido, optionally substituted aryl, optionally substituted heteroaryl, carbonyl, carboxyl, optionally substituted ether, optionally substituted thioether, optionally substituted alkylsulfonyl, optionally substituted arylsulfonyl, optionally substituted ketone, optionally substituted ester, and the like.

Steroidal compounds can be naturally occurring, semi-synthetic, or fully synthetic. The enone moiety can be present in the naturally occurring steroidal compound (e.g., testosterone) or it may be introduced synthetically, e.g., an enone of cyclopamine as shown below:

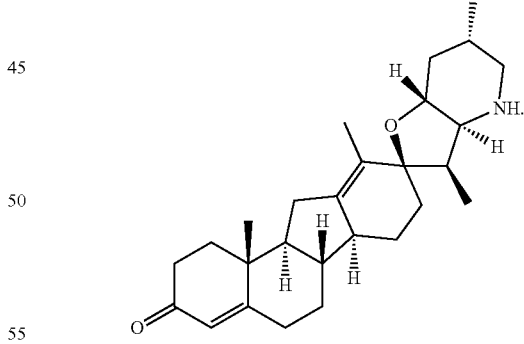

Examples of steroidal compounds that have enone moieties or that can be modified to contain enone moieties include, but are not limited to, cholestanes, cholanes, pregnanes, androstanes, estranges, progestagens, bras sinosteroids, bufadienolides, cardenolides, cucurbitacins, ecdysteroids, sapogenins, steroid alkaloids, anabolic steroids, withasteroids, bile acids, hormonal steroids (e.g., sexual hormones, corticosteroids, neurosteroids), glucocorticoids, mineralocorticoids, and the like. Examples include compounds having the following general structures:

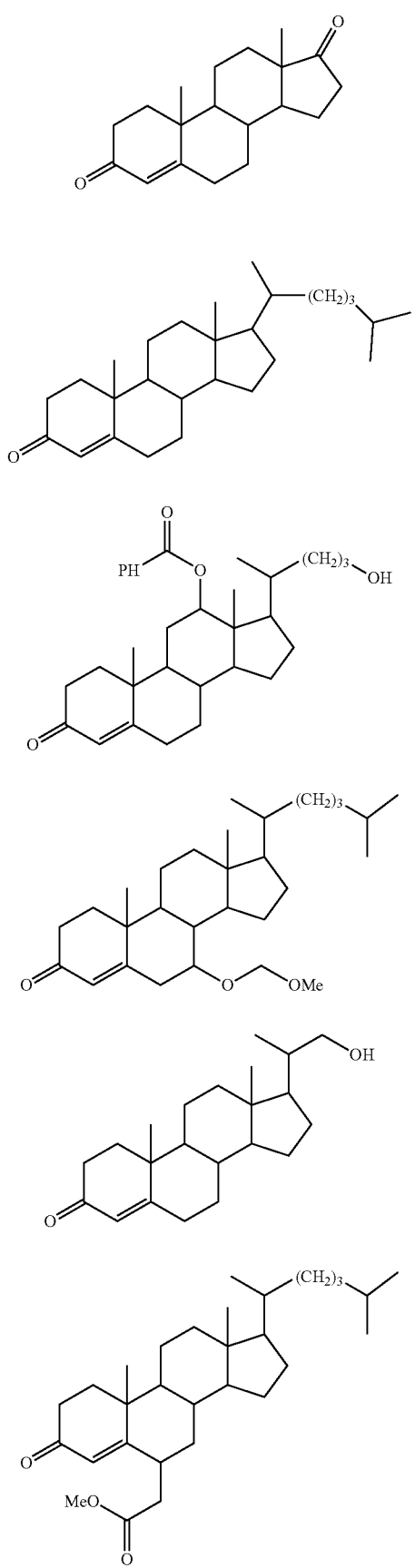
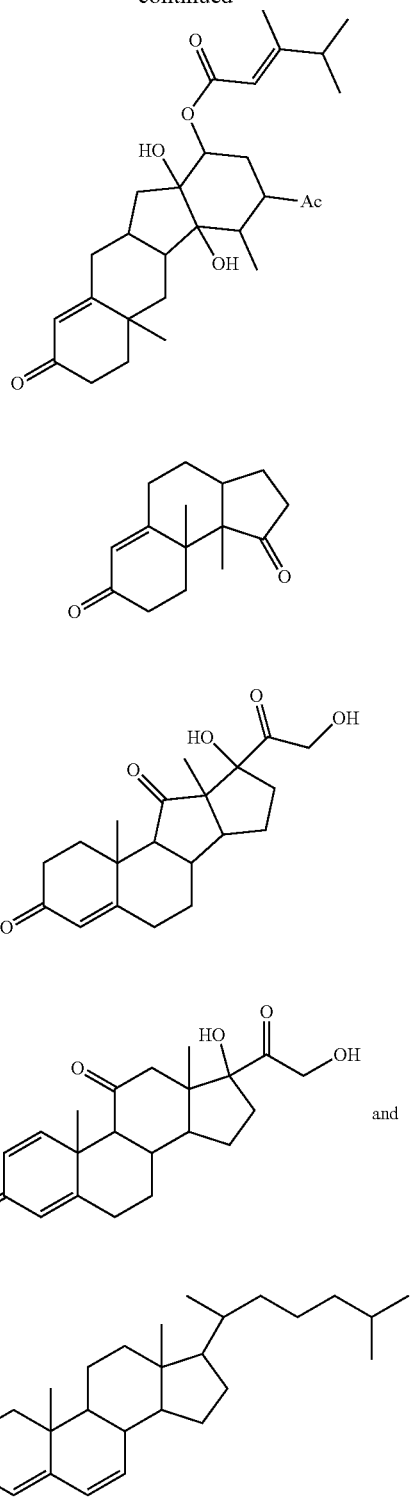
Further examples of steroidal compounds that can be reduced according to the present invention include compounds of Formula A:

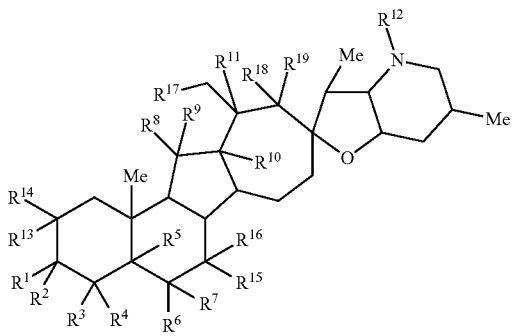

A or a pharmaceutically acceptable salt thereof; wherein $R^1$ and $R^2$ taken together with the carbon to which they are bound form a carbonyl;

$R^8$ is H, alkyl, alkenyl, alkynyl, aryl, cycloalkyl, heterocycloalkyl, aralkyl, heteroaryl, heteroaralkyl, halide, sulfhydryl, alkylthio, arylthio, aralkylthio, hydroxyl, alkoxyl, aryloxy, acyloxy, amino, alkylamino, arylamino, acylamino, aralkylamino, nitro, acylthio, carboxamide, sulfonamide, carboxyl, nitrile, sulfate, —OP(L)(OR$^{20}$)$_2$, —X—C(L)-R$^{21}$ or —X—C(L)-X—R$^{21}$;

X is O or NR wherein R is H, alkyl, alkenyl, alkynyl, aryl, cycloalkyl or aralkyl;

L is O or S;

$R^9$ is H, alkyl, alkenyl, alkynyl, aryl, cycloalkyl, heterocycloalkyl, aralkyl, alkoxyl, aryloxy, acyloxy, halide, sulfhydryl, alkylthio, arylthio, aralkylthio, hydroxyl, amino, alkylamino, arylamino, acylamino, aralkylamino, heteroaryl, or heteroaralkyl;

$R^4$ and $R^5$ taken together form a double bond;

$R^{10}$ and $R^{11}$ taken together form a double bond or form a group represented by 1b
wherein Z is NR$^{21}$, O, or C(R$^{23}$)(R$^{23}$);

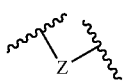

1b $R^{12}$ is H, alkyl, alkenyl, alkynyl, aryl, cycloalkyl, heterocycloalkyl, hydroxyl, aralkyl, heteroaryl, heteroaralkyl, haloalkyl, alkoxyl, —C(O)R$^{21}$, —CO$_2$R$^{21}$, —SO$_2$R$^{21}$, —C(O)N(R$^{21}$)(R$^{21}$), —[C(R$^{21}$)$_2$]$_q$—R$^{21}$, —[(W)—N(R$^{21}$)C(O)]$_q$R$^{21}$, —[(W)—C(O)]$_q$R$^{21}$, —[(W)—C(O)O]$_q$R$^{21}$, —[(W)—OC(O)]$_q$R$^{21}$, —[(W)—SO$_2$]$_q$R$^{21}$, —[(W)—N(R$^{21}$)SO$_2$]$_q$R$^{21}$, —[(W)—C(O)N(R$^{21}$)]$_q$R$^{21}$, —[(W)—O]$_q$R$^{21}$, —[(W)—N(R$^{21}$)]$_q$R$^{21}$, or —[(W)—S]$_q$R$^{21}$;

W is a diradical, and q is 1, 2, 3, 4, 5, or 6;

$R^{15}$, $R^{16}$, and $R^{17}$ are independently H, alkoxyl, aryloxy, acyloxy, halide, hydroxyl, amino, alkylamino, arylamino, acylamino, aralkylamino; or $R^{15}$ and $R^{16}$ taken together, along with the carbon to which they are bonded, form —C(O)— or —C(S)—;

$R^{18}$ and $R^{19}$ are independently H, alkyl, aralkyl, halide, amido, or ester;

$R^{20}$ is H, alkyl, alkenyl, alkynyl, aryl, cycloalkyl, heterocycloalkyl, aralkyl, heteroaryl, or heteroaralkyl; or any two occurrences of R$^{20}$ on the same substituent can be taken together to form a 4-8 membered optionally substituted ring;

$R^{21}$ is H, alkyl, alkenyl, alkynyl, aryl, cycloalkyl, heterocycloalkyl, aralkyl, heteroaryl, heteroaralkyl or —[C(R$^{20}$)$_2$]$_p$—R$^{25}$ wherein p is 0-6; or any two occurrences of R$^{21}$ on the same substituent can be taken together to form a 4-8 membered optionally substituted ring;

$R^{23}$ is H, alkyl, alkenyl, alkynyl, aryl, cycloalkyl, heterocycloalkyl, aralkyl, heteroaryl, heteroaralkyl, halide, alkoxyl, aryloxy, acyloxy, silyloxy, nitrile, —C(O)R$^{21}$, —CO$_2$R$^{21}$, —SO$_2$R$^{21}$, and —C(O)N(R$^{21}$)$_2$; and $R^{25}$ is hydroxyl, acylamino, —N(R$^{20}$)COR$^{20}$, —N(R$^{20}$)C(O)OR$^{20}$, —N(R$^{20}$)SO$_2$(R$^{20}$), —COR$^{20}$N(R$^{20}$)$_2$, —OC(O)R$^{20}$N(R$^{20}$)(R$^{20}$), —SO$_2$N(R$^{20}$)(R$^{20}$), —N(R$^{20}$)(R$^{20}$), —COOR$^{20}$, —C(O)N(OH)(R$^{21}$), —OS(O)$_2$OR$^{20}$, —S(O)$_2$OR$^{20}$, —OP(L)(OR$^{20}$)(OR$^{20}$), —NP(O)(OR$^{20}$)(OR$^{20}$), or —P(O)(OR$^{20}$)(OR$^{20}$).

Further examples of steroidal compounds that can be reduced according to the present invention include compounds of Formula B:

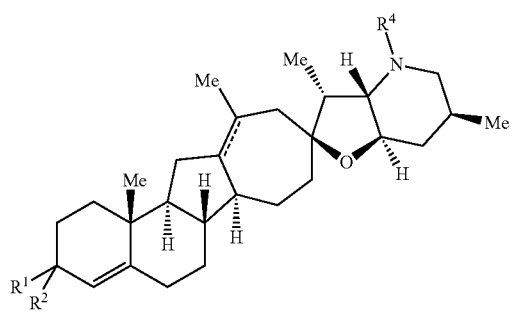

B or a pharmaceutically acceptable salt thereof; wherein $R^1$ and $R^2$ taken together with the carbon to which they are bound form a carbonyl;

$R^4$ is H, alkyl, alkenyl, alkynyl, aryl, cycloalkyl, heterocycloalkyl, aralkyl, heteroaryl, heteroaralkyl, haloalkyl, —OR$^5$, —C(O)R$^5$, —CO$_2$R$^5$, —SO$_2$R$^5$, —C(O)N(R$^5$)(R$^5$), —[C(R)$_2$]$_q$—R$^5$, —[(W)—N(R)C(O)]$_q$R$^5$, —[(W)—C(O)]$_q$R$^5$, —[(W)—C(O)O]$_q$R$^5$, —[(W)—OC(O)]$_q$R$^5$, —[(W)—SO$_2$]$_q$R$^5$, —[(W)—N(R$^5$)SO$_2$]$_q$R$^5$, —[(W)—C(O)N(R$^5$)]$_q$R$^5$, —[(W)—O]$_q$R$^5$, —[(W)—N(R)]$_q$R$^5$, —W—NR$^5$$_3$$^+$X$^-$ or —[(W)—S]$_q$R$^5$;

each W is independently a diradical;

each q is independently 1, 2, 3, 4, 5, or 6;

X$^-$ is a halide;

each $R^5$ is independently H, alkyl, alkenyl, alkynyl, aryl, cycloalkyl, heterocycloalkyl, aralkyl, heteroaryl, heteroaralkyl or —[C(R)$_2$]$_p$—R$^6$; wherein p is 0-6; or any two occurrences of R$^5$ can be taken together to form a 4-8 membered optionally substituted ring which contains 0-3 heteroatoms selected from N, O, S, and P;

each $R^6$ is independently hydroxyl, —N(R)COR, —N(R)C(O)OR, —N(R)SO$_2$(R), —C(O)N(R)$_2$, —OC(O)N(R)(R), —SO$_2$N(R)(R), —N(R)(R), —COOR, —C(O)N(OH)(R), —OS(O)$_2$OR, —S(O)$_2$OR, —OP(O)(OR)(OR), —NP(O)(OR)(OR), or —P(O)(OR)(OR); and each R is independently H, alkyl, alkenyl, alkynyl, aryl, cycloalkyl or aralkyl.

Examples of compounds that may be reduced according to the invention include:

9
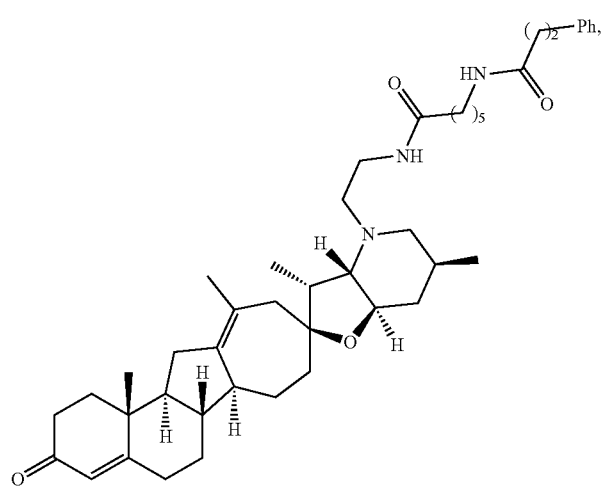
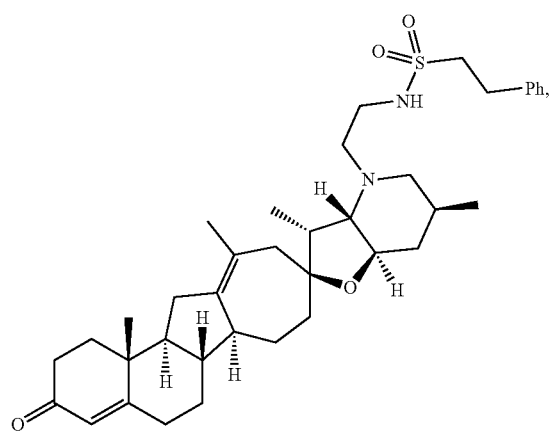
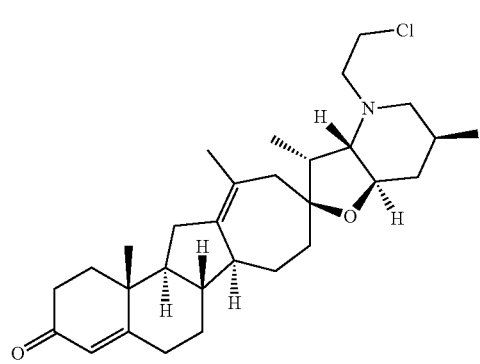
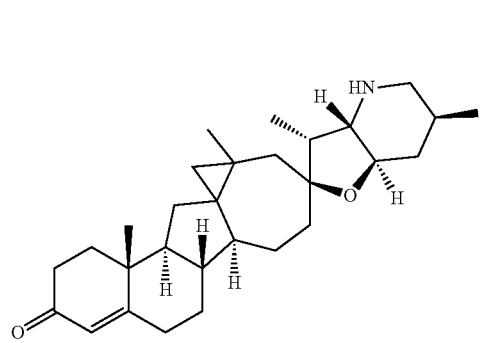
10
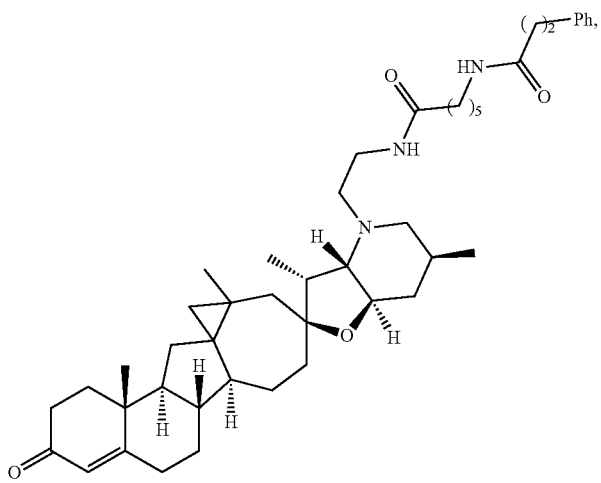
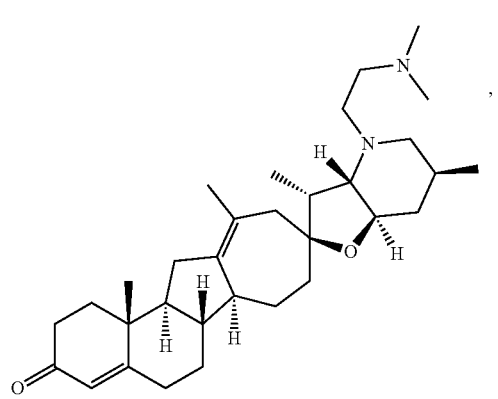
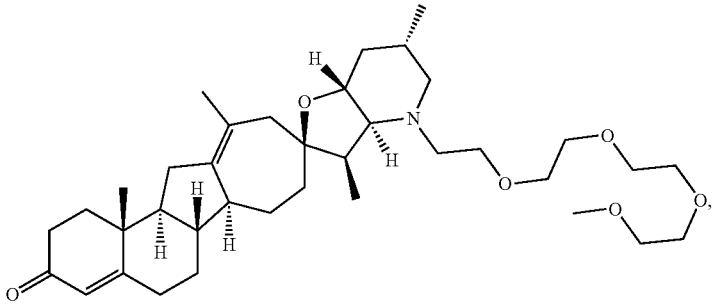
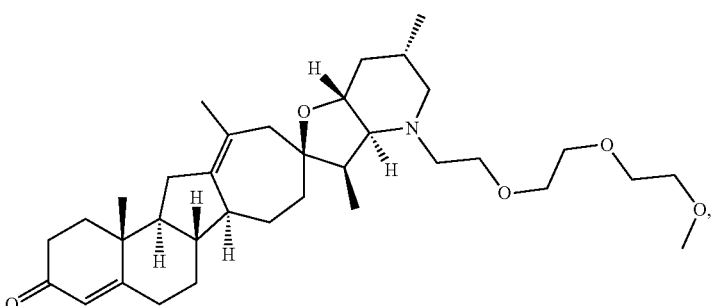

-continued
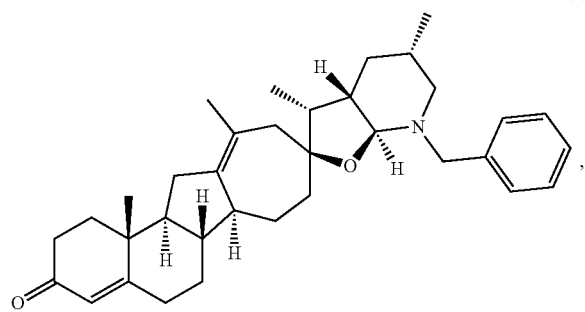
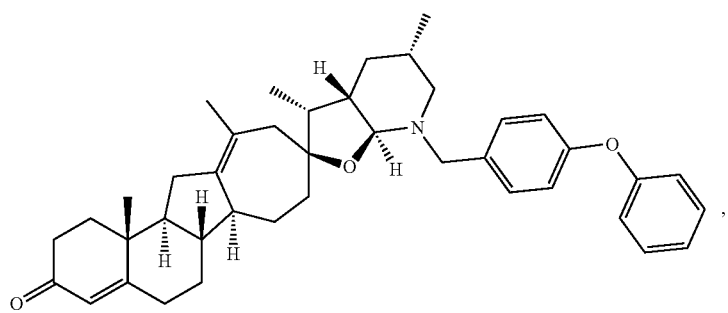
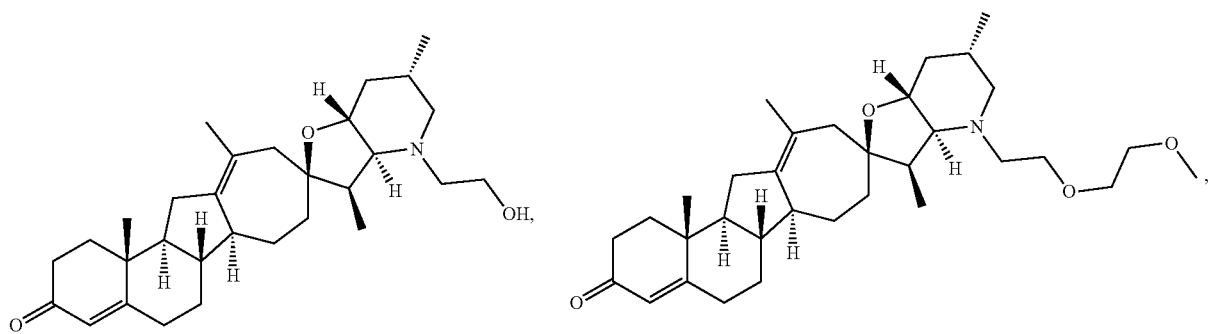
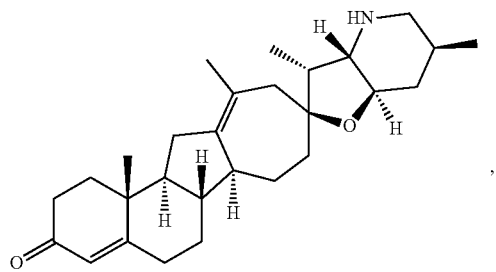
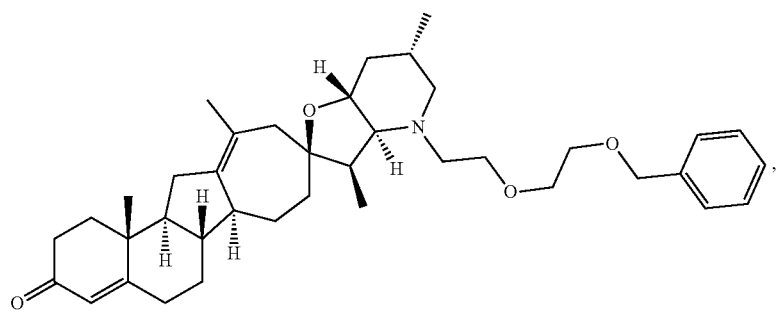

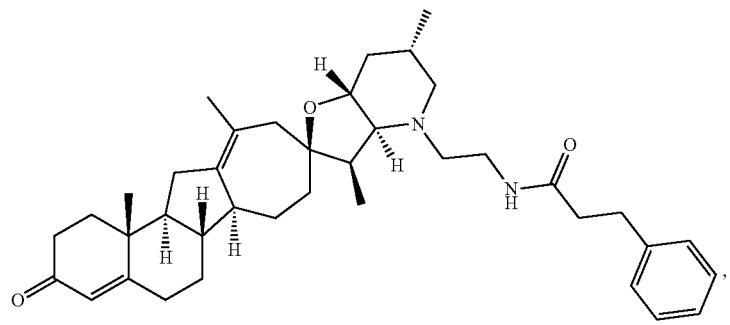
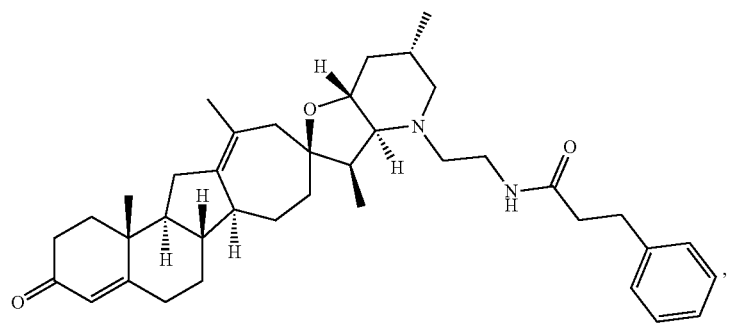
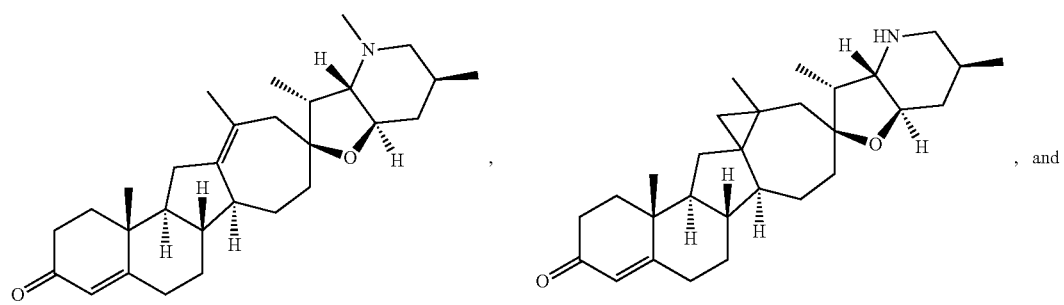
, and
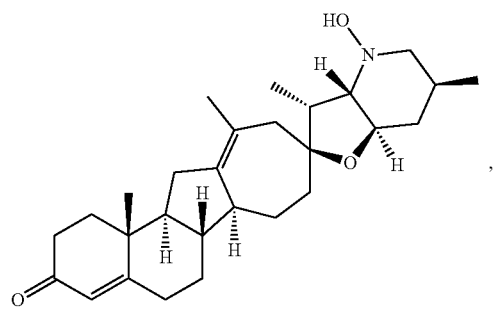
,
and pharmaceutically acceptable salts thereof.

In one aspect, the invention provides a method of making a mixture of compounds of formulae II and III:

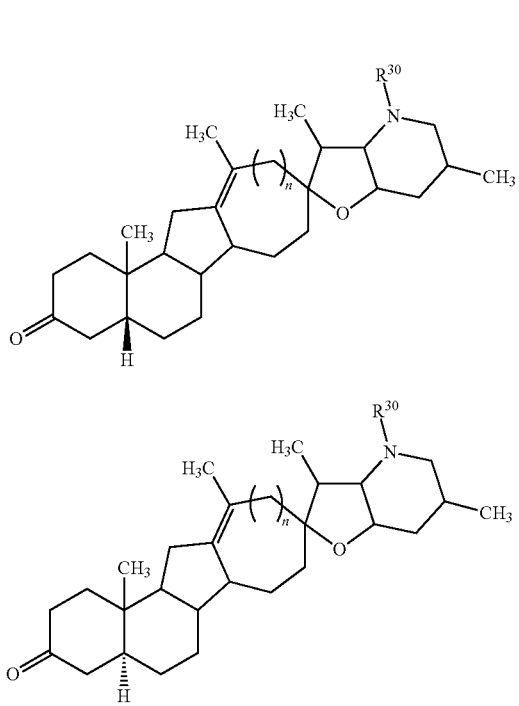

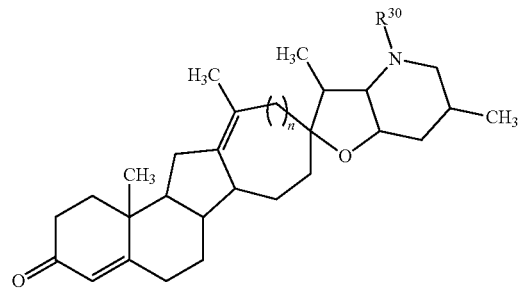

or a pharmaceutically acceptable salt thereof, wherein:

n is 0 or 1;

$R^{30}$ is H, alkyl, alkenyl, alkynyl, aryl, cycloalkyl, heterocycloalkyl, aralkyl, heteroaryl, heteroaralkyl, haloalkyl, —$OR^{31}$, —$C(O)R^{31}$, —$CO_2R^{31}$, —$SO_2R^{31}$, —$C(O)N(R^{31})(R^{31})$, —$[C(R)_2]_q$—$R^{31}$, —$[(W)$—$N(R)C(O)]_qR^{31}$, —$[(W)$—$C(O)]_qR^{31}$, —$[(W)$—$C(O)O]_qR^{31}$, —$[(W)$—$OC(O)]_qR^3$, —$[(W)$—$SO_2]_qR^{31}$, —$[(W)$—$N(R^{31})SO_2]_qR^{31}$, —$[(W)$—$C(O)N(R^{31})]_qR^{31}$, —$[(W)$—$O]_qR^{31}$, —$[(W)$—$N(R)]_qR^{31}$, —$W$—$(NR^{31})_3{}^+X^-$ or —$[(W)$—$S]_qR^{31}$;

W, at each occurrence, independently is an alkylene group;

q, at each occurrence, independently is 1, 2, 3, 4, 5, or 6;

$X^-$ is a halide;

$R^{31}$, at each occurrence, independently is H, alkyl, alkenyl, alkynyl, aryl, cycloalkyl, heterocycloalkyl, aralkyl, heteroaryl, heteroaralkyl or —$[C(R)_2]_p$—$R^{32}$;

or any two occurrences of $R^{31}$ taken together with the atom to which they are bound form an optionally substituted 4-8 membered ring that contains 0-3 heteroatoms selected from N, O and S;

p is 0-6;

each $R^{32}$ is independently hydroxyl, —N(R)COR, —N(R)C(O)OR, —N(R)SO$_2$(R), —C(O)N(R)$_2$, —OC(O)N(R)(R), —SO$_2$N(R)(R), —N(R)(R), —COOR, —C(O)N(OH)(R), —OS(O)$_2$OR, —S(O)$_2$OR, —OP(O)(OR)(OR), —NP(O)(OR)(OR), or —P(O)(OR)(OR); and each R is independently H, alkyl, alkenyl, alkynyl, aryl, cycloalkyl or aralkyl; the method comprising treating a solution or suspension of compound of formula IV:

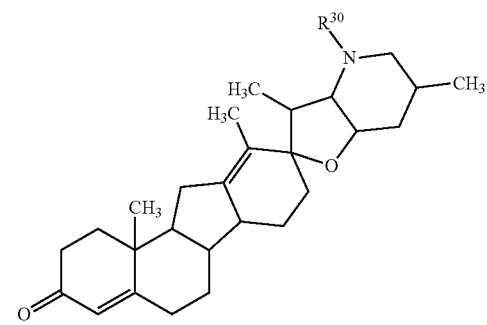

or a pharmaceutically acceptable salt thereof, in a solvent with hydrogen gas in the presence of a catalyst and a substituted pyridine. In some embodiments, an excess of the compound of formula II is produced compared to the compound of formula III (e.g., the ratio of the compound of formula II to compound of formula III is at least about 2:1, about 3:1, about 5:1, about 10:1, about 20:1, about 25:1, about 30:1, about 40:1, about 50:1, about 60:1, about 70:1, about 80:1, about 90:1, about 95:1, or greater than about 99:1). The substituted pyridine can be a 3-substituted pyridine (e.g., 3-picoline, 3-methoxypyridine, 3-ethylpyridine, 3-n-butylpyridine, 3-isobutylpyridine, 3-hydroxypyridine, 3-aminopyridine, or 3-dimethylaminopyridine). In some embodiments, the solvent is the substituted pyridine (e.g., 3-picoline). The catalyst can be a palladium catalyst (e.g., palladium on carbon). In some embodiments, n is 0, i.e., the compound of formula IV has the following structure:

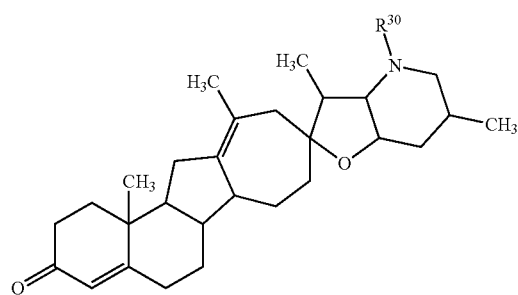

In other embodiments, n is 1, i.e., the compound of formula IV has the following structure:

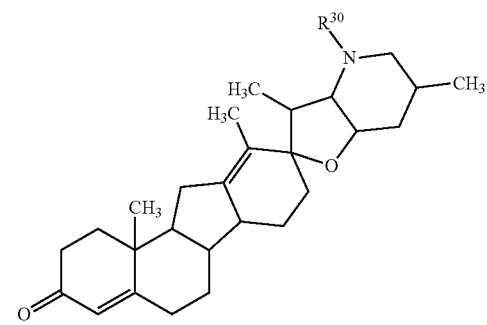

In some embodiments, $R^{30}$ is H, i.e., the compound of formula IV has one of the following structures:

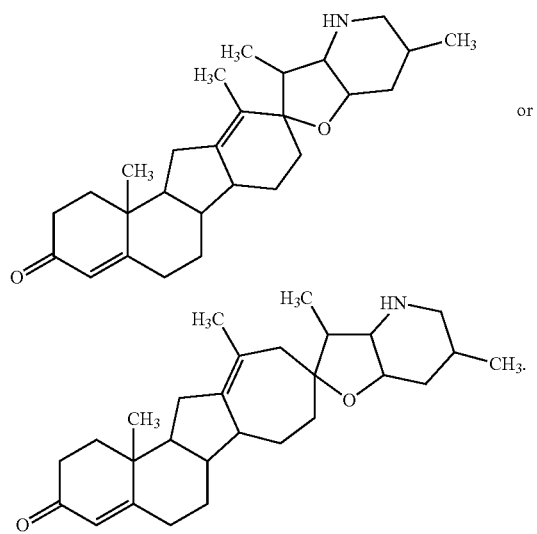 or

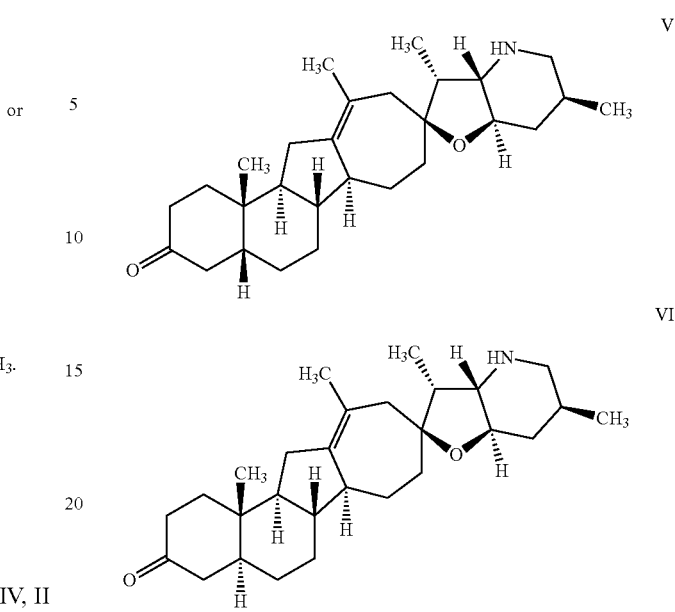

In some embodiments, the compounds of formulae IV, II and III have the following absolute chemistry:

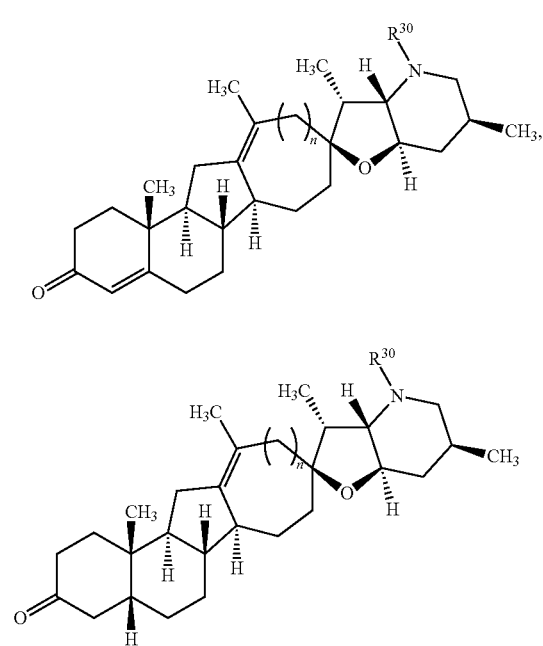

In another aspect, the invention provides a method of making a mixture of compounds V and VI:

or a pharmaceutically acceptable salt thereof, the method comprising treating a solution or suspension of compound VII:

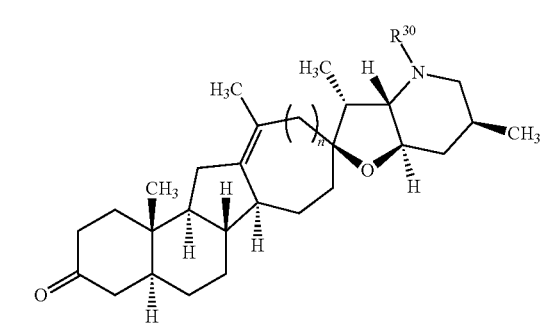

or a pharmaceutically acceptable salt thereof, in a solvent with hydrogen gas in the presence of a palladium catalyst and a substituted pyridine. In some embodiments, an excess of the compound of formula V is produced compared to the compound of formula VI (e.g., the ratio of the compound of formula V to compound of formula VI is at least about 2:1, about 3:1, about 5:1, about 10:1, about 20:1, about 25:1, about 30:1, about 40:1, about 50:1, about 60:1, about 70:1, about 80:1, about 90:1, about 95:1, or greater than about 99:1). The substituted pyridine can be a 3-substituted pyridine (e.g., 3-picoline, 3-methoxypyridine, 3-ethylpyridine, 3-n-butylpyridine, 3-isobutylpyridine, 3-hydroxypyridine, 3-aminopyridine, or 3-dimethylaminopyridine). Alternatively, the substituted pyridine can be a 4-substituted pyridine (e.g., 4-picoline, 4-methoxypyridine, 4-aminopyridine, or 4-dimethylaminopyridine). In some embodiments, the solvent is the substituted pyridine (e.g., 3-picoline). The catalyst can be a palladium catalyst (e.g., palladium on carbon). The method can include the further steps of adding an aqueous solution of an acid (e.g., HCl, HBr, HI, H$_2$SO$_4$, H$_3$PO$_4$, methanesulfonic acid, ethanesulfonic acid, benzenesulfonic acid, toluenesulfonic acid, citric acid, benzoic acid, formic acid, acetic acid, propionic acid, gluconic acid, lactic acid, oxalic acid, trifluoroacetic acid, or tartaric acid) and isolating the salt of compounds V and/or VI. In some embodiments, the citric acid salts of compounds V and/or VI are prepared and isolated.

In another aspect, the method provides compounds of formulae IX and X:

IX

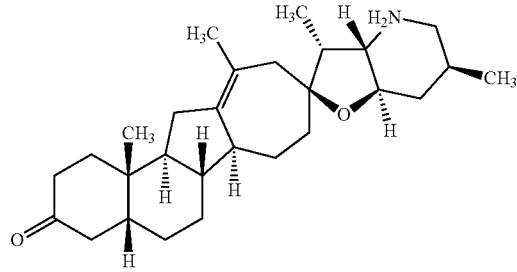

X

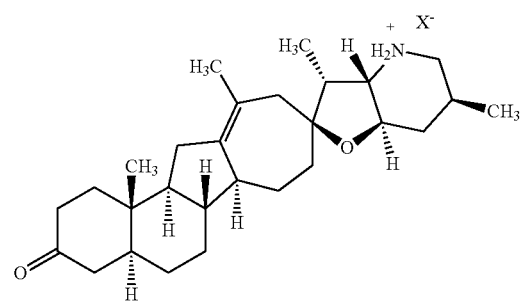

and mixtures thereof, wherein X$^-$ is the conjugate base of a pharmaceutically acceptable acid (e.g., chloride, bromide, sulfate, methanesulfonate or citrate). In some embodiments, X$^-$ is citrate. When compounds of formulae IX and X are present in a mixture, an excess of compound IX can be present compared to compound X. For example, the ratio of the compound of formula IX to compound of formula X can be at least about 2:1, about 3:1, about 5:1, about 10:1, about 20:1, about 25:1, about 30:1, about 40:1, about 50:1, about 60:1, about 70:1, about 80:1, about 90:1, about 95:1, or greater than about 99:1.

In another aspect, the invention provides a method of making a compound of formula XV:

XV

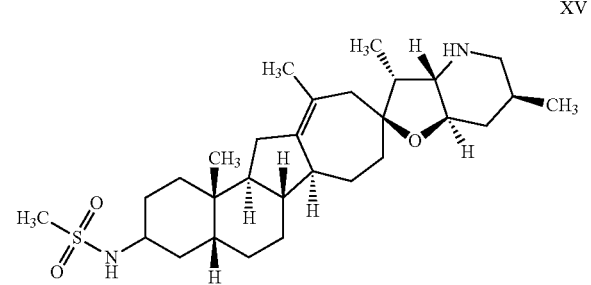

comprising the steps of:
(a) treating a compound of formula IX:

IX

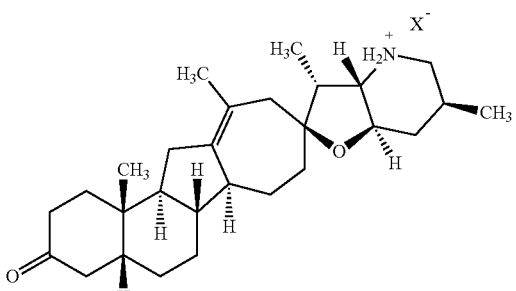

wherein X$^-$ is the conjugate base of a pharmaceutically acceptable salt (e.g., chloride, bromide, sulfate, methanesulfonate or citrate), with an amine protecting reagent to produce a compound of formula XI:

XI

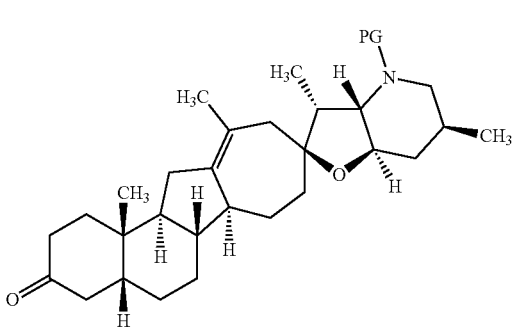

wherein PG is an amine protecting group;
(b) treating the compound of formula XI with a reducing agent to produce an alcohol of formula XII:

XII

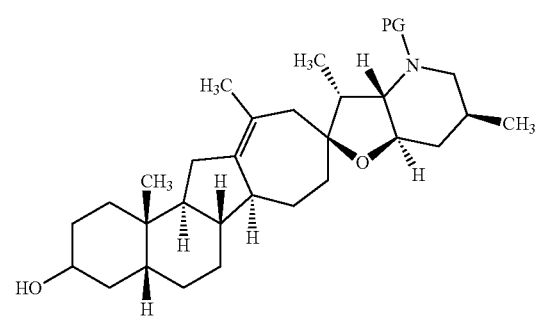

(c) converting the alcohol of formula XII to an amine of formula XIII:

XIII

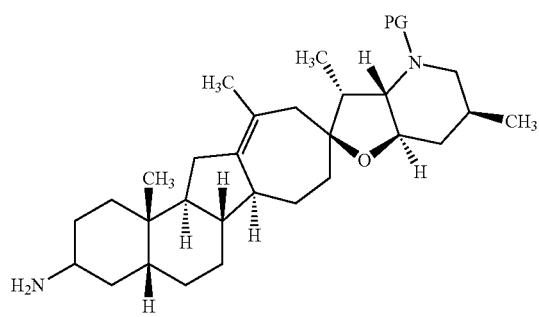

(d) treating the amine of formula XIII with a sulfonylating agent (e.g., methanesulfonyl chloride) to produce a sulfonamide of formula XIV:

XIV

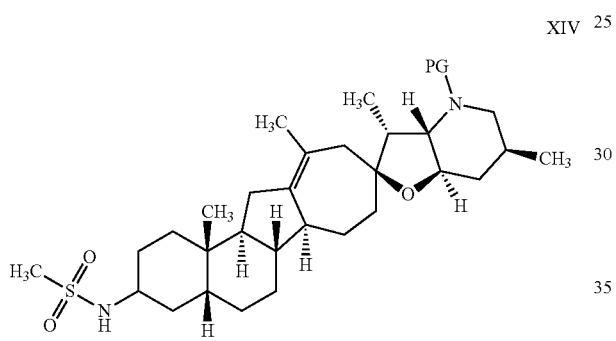

and (e) deprotecting the amine of the compound of formula XIV to produce the compound of formula XV.

The protecting group (PG) can be any suitable amine protecting group known in the art, including carbamates (e.g., carbobenzyloxy (Cbz), t-butyloxycarbonyl (BOC), allyloxycarbonyl (Alloc), 9-fluoenylmethyl (Fmoc), and the like), amide-forming groups (e.g., acetyl, trifluoroacetyl, benzoyl, and the like), silyl groups and benzyl. Suitable amine protecting reagents include chlorides, acid chlorides, anhydrides (including mixed anhydrides) and other activated species that will react with the amine and deliver the protecting group. Examples include BOC—Cl, (BOC)$_2$O, Cbz-Cl, (Cbz)$_2$O, Cbz-O-benzotriazole, Alloc-Cl, (Alloc)$_2$O, Fmoc-Cl, (Fmoc)$_2$O, benzylchloride, and the like. See, e.g., Greene, *Protective Groups in Organic Synthesis*.

In step (b), the reducing agent can be any reducing agent known in the art that will reduce a ketone to an alcohol. Examples of suitable reducing agents include boron reducing agents (e.g., potassium tri-sec-butylborohydride, sodium borohydride), and metallic hydrides (e.g., lithium aluminum hydride). See, e.g., March, *Advanced Organic Chemistry*.

Step (c) can comprise the steps of (1) converting the alcohol to a leaving group to produce a compound of formula XVI:

XVI

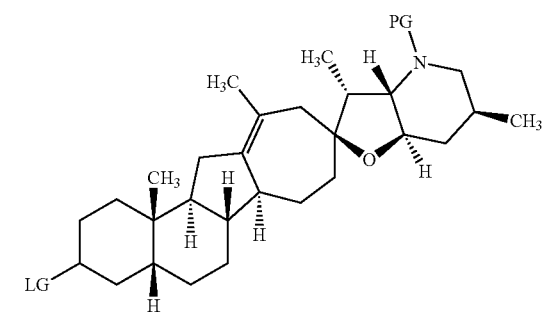

wherein LG is a leaving group, followed by (2) treating the compound of formula XVI with an azide reagent to produce a compound of formula XVII:

XVII

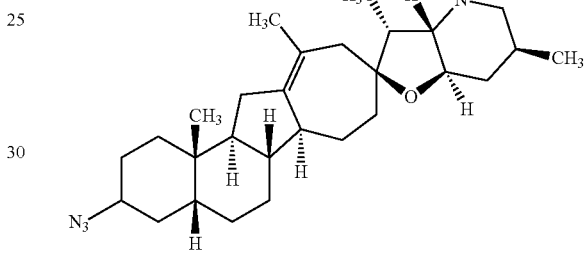

and (3) treating the compound of formula XVII with a reducing agent to form the amine of formula XIII.

The leaving group (LG) can be a sulfonate group (e.g., methanesulfonate, benzenesulfonate, toluenesulfonate, and the like), a halogen (e.g., Cl, Br) or any other suitable leaving group known in the art. The leaving group can be formed by treatment with the corresponding sulfonyl chloride (e.g., methanesulfonyl chloride) or with an acid halide (e.g., HBr). See, e.g., March, *Advanced Organic Chemistry*.

The azide reagent can be, for example, sodium azide, potassium azide, methanesulfonyl azide, p-toluenesulfonyl azide, p-acetamidobenzenesulfonyl azide, 4-carboxybenzenesulfonyl azide, p-dodecylbenzenesulfonyl azide, or trimethylsilyl azide. See, e.g., March, *Advanced Organic Chemistry*. In some embodiments, the azide reagent is sodium azide.

Any suitable reducing agent known in the art may be used to reduce the azide of the compound of formula XVII to the amine of formula XIII. Examples of reducing agents include lithium aluminum hydride, sodium borohydride, and triphenylphosphine. The azide can also be reduced to the amine by catalytic hydrogenation. See, e.g., March, *Advanced Organic Chemistry*. In some embodiments, the azide is reduced using triphenylphosphine.

The amine protecting group PG can be removed by standard conditions known in the art. The particular deprotection conditions will vary depending upon the nature of the protecting group. For example, a Cbz group can be removed by hydrogenation using a catalyst (e.g., a palladium catalyst such as Pd/C or palladium black) and hydrogen gas or another hydrogen donor (e.g., cyclohexene, 1,4-cyclohexadiene, formic acid). See, e.g., Greene, *Protective Groups in Organic Synthesis*.

The order of one or more steps in the synthesis of compound XV from compound IX can be changed, provided that the change results in the complete synthesis of compound XV. For example, introduction of the amine protecting group PG can occur at any time in the synthesis prior to reduction of the azide XVII to produce amine XIII. Compound IX can be treated with a reducing agent to produce an alcohol of formula XIIa:

XIIa

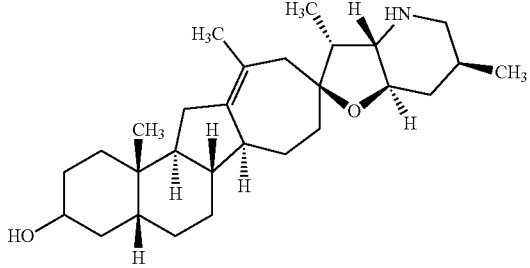

Compound XIIa can then be treated with the amine protecting agent to form compound XII. Alternatively, the alcohol moiety of compound XIIa can be converted to a leaving group to produce a compound of formula XVIa:

XVIa

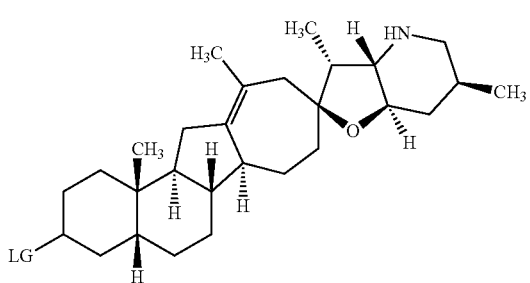

Compound XVIa can then be treated with the amine protecting agent to form compound XVI. Alternatively, compound XVIa can be treated with an azide reagent to produce a compound of formula XVIIa:

XVIIa

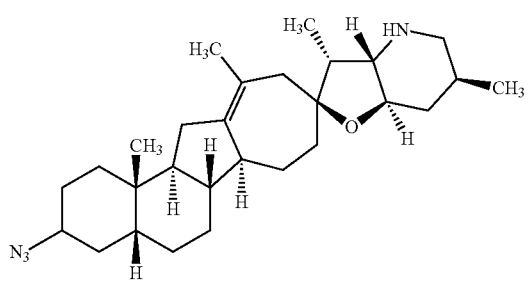

Compound XVIIa can then be treated with the amine protecting group to form a compound of formula XVII.

In some embodiments, the method further comprises the step of treating the compound of formula XV with an acid to produce a compound of formula XIX:

XIX

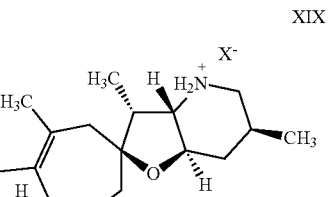

wherein $X^-$ is the conjugate base of a pharmaceutically acceptable acid (e.g., chloride, bromide, sulfate, methanesulfonate or citrate). In some embodiments, the acid is HCl and $X^-$ is chloride.

In some embodiments, the compound of formula XV has the following absolute stereochemistry:

XVa

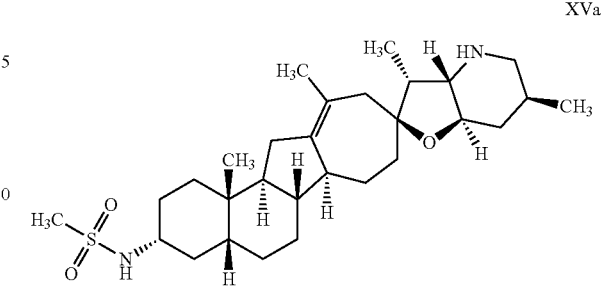

In other embodiments, the method produces a mixture of compounds having the structures with the following absolute stereochemistry:

XVa

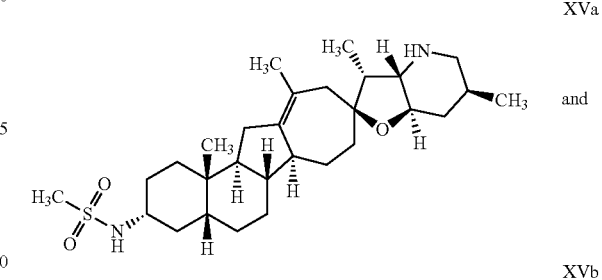

and

XVb

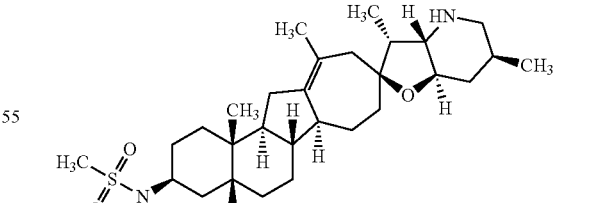

In some instances, compound XVa is produced in excess of compound XVb (e.g., the ratio of XVa to XVb is about 2:1, about 3:1, about 5:1, about 10:1, about 20:1, about 25:1, about 30:1, about 40:1, about 50:1, about 60:1, about 70:1, about 80:1, about 90:1, about 95:1, or greater than about 99:1).

In another aspect, the invention provides a mixture of a compound of formula V:

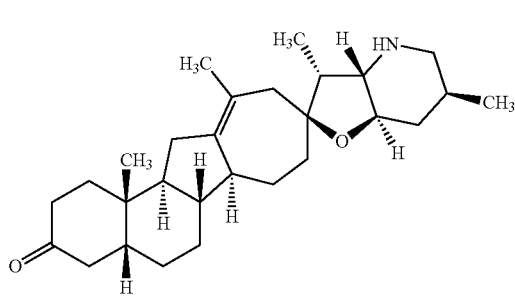

or a pharmaceutically acceptable salt thereof, and a compound of formula 2a or a pharmaceutically acceptable salt thereof:

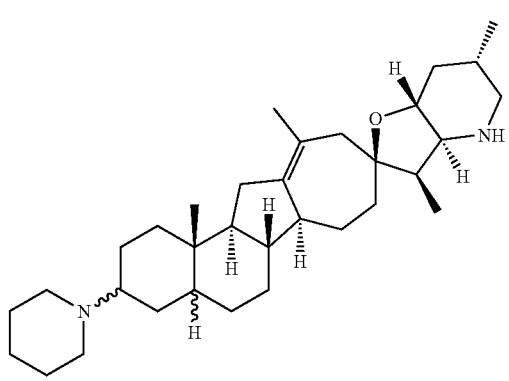

In some embodiments, compound 2a is present in less than about 10%, about 5%, about 2%, about 1%, about 0.5%, about 0.1%, or about 0.01%.

In another aspect, the invention provides a mixture of a compound of formula V:

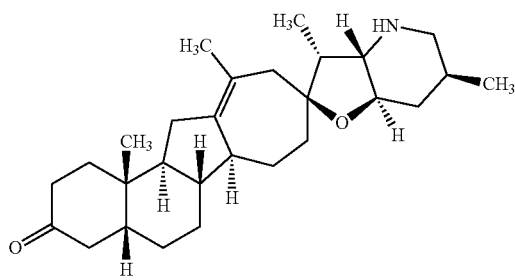

or a pharmaceutically acceptable salt thereof, and a compound of formula 2b or a pharmaceutically acceptable salt thereof:

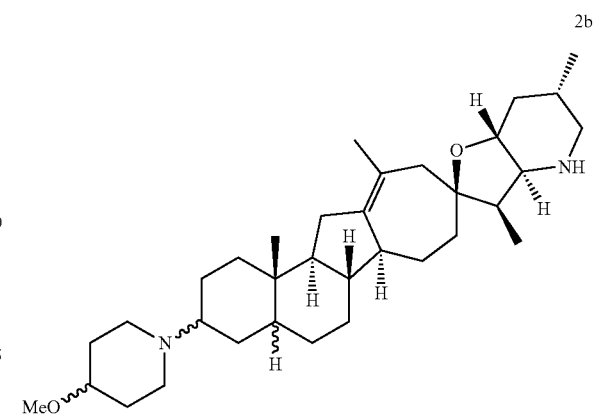

In some embodiments, compound 2b is present in less than about 10%, about 5%, about 2%, about 1%, about 0.5%, about 0.1%, or about 0.01%.

In yet another aspect, the invention provides a mixture of a compound of formula V:

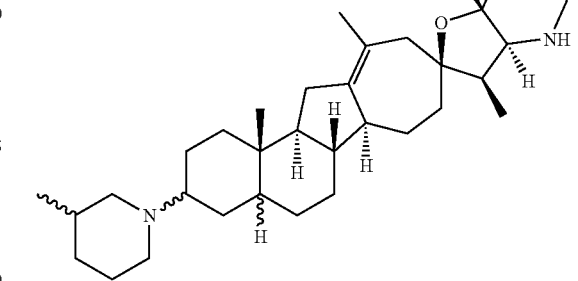

or a pharmaceutically acceptable salt thereof, and a compound of formula 2c or a pharmaceutically acceptable salt thereof:

2c

In some embodiments, compound 2c is present in less than about 10%, about 5%, about 2%, about 1%, about 0.5%, about 0.1%, or about 0.01%.

In another aspect, the invention provides a mixture of compounds V and VI:

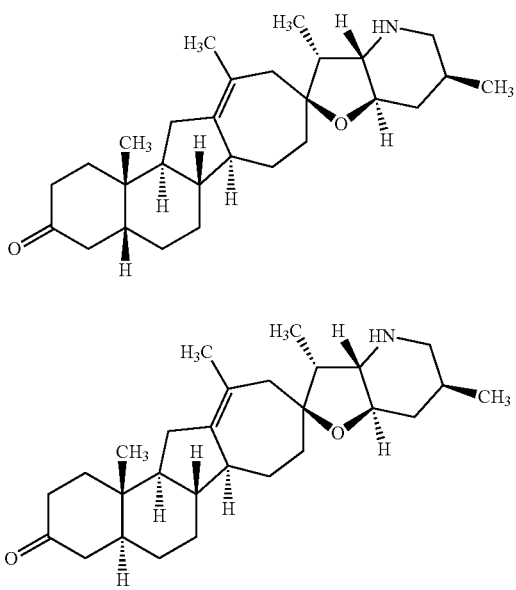

V

VI or a pharmaceutically acceptable salt thereof, and one of compounds 2a, 2b or 2c or a pharmaceutically acceptable salt thereof. In some embodiments, compound 2a, 2b or 2c is present in less than about 10%, about 5%, about 2%, about 1%, about 0.5%, about 0.1%, or about 0.01%.

In another aspect, the invention provides a mixture of compound XVa:

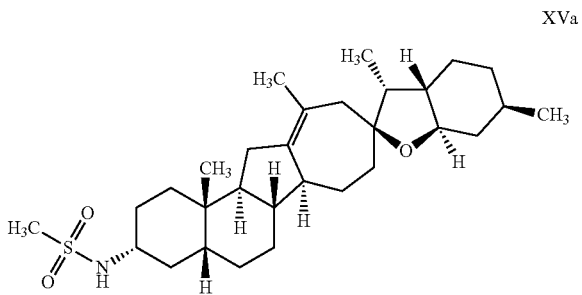

XVa or a pharmaceutically acceptable salt thereof, and one of compounds 2a, 2b or 2c or a pharmaceutically acceptable salt thereof. In some embodiments, compound 2a, 2b or 2c is present in less than about 10%, about 5%, about 2%, about 1%, about 0.5%, about 0.1%, or about 0.01%. In some embodiments, the pharmaceutically acceptable salt is a hydrochloride salt.

The term "heteroatom" refers to an atom of any element other than carbon or hydrogen. Illustrative heteroatoms include nitrogen, oxygen, and sulfur.

The term "alkyl" refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 10 or fewer carbon atoms in its backbone (e.g., $C_1$-$C_{10}$ for straight chain, $C_3$-$C_{10}$ for branched chain). In certain embodiments, a straight chain or branched chain alkyl has about 6 or fewer carbon atoms in its backbone (e.g., $C_1$-$C_6$ for straight chain, $C_3$-$C_6$ for branched chain). Cycloalkyls have from about 3 to about 10 carbon atoms in their ring structure, e.g., about 3, 4, 5, 6 or 7 carbons in the ring structure. Alkyl groups, unless otherwise specified, may optionally be substituted by replacing one or more hydrogens with a suitable substituent. Suitable substituents for alkyl groups include halogen, =O, =N—CN, =N—OR', =NR', OR', NR'$_2$, SR', SO$_2$R', SO$_2$NR'$_2$, NR'SO$_2$R', NR'CONR'$_2$, NR'COOR', NR'COR', CN, COOR', CONR'$_2$, OOCR', COR', and NO$_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$aryl, $C_5$-$C_{10}$heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; and wherein two R' on the same substituent or on adjacent atoms can be linked to form a 3-7 membered ring optionally containing up to three heteroatoms selected from N, O and S.

Unless the number of carbons is otherwise specified, "lower alkyl" refers to an alkyl group, as defined above, having from one to six carbon atoms in its backbone structure. Likewise, "lower alkenyl" and "lower alkynyl" have similar chain lengths.

The terms "alkenyl" and "alkynyl" refer to straight-chain or branched unsaturated aliphatic groups that contain at least one double or triple bond respectively and may contain a mixture of both double and triple bonds. Alkenyl and alkynyl groups have about 10 or fewer carbon atoms in their backbones (e.g., $C_2$-$C_{10}$ for straight chain and $C_4$-$C_{10}$ for branched chain). In certain embodiments, alkenyl and alkynyl groups have about 6 or fewer carbon atoms in their backbones (e.g., $C_1$-$C_6$ for straight chain and $C_4$-$C_6$ for branched chain). Alkenyl and alkynyl groups can be optionally substituted by the same substituents described above for alkyl groups.

The term "aryl" refers to 5-, 6- and 7-membered single-ring aromatic groups that may include from zero to four heteroatoms. Examples of aryl include benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl". The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes fused polycyclic ring systems wherein at least one of the rings is aromatic, e.g., the other cyclic rings may be cycloalkyls, cycloalkenyls, cycloalkynyls, aryls and/or heterocyclyls.

The term "aralkyl" refers to an alkyl group substituted with an aryl group (e.g., an aromatic or heteroaromatic group).

The terms "heterocycle", "heteroaryl", or "heterocyclic group" refer to 3- to 10-membered ring structures, alternatively 3- to 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle" refers to an aromatic or non-aromatic ring in which each atom of the ring is carbon.

The terms "amine", "amino" and "ammonium" refer to both unsubstituted and substituted amines, e.g., a moiety that may be represented by the general formulas:

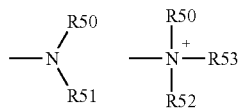

wherein R50, R51 and R52 each independently represent a hydrogen, an alkyl, an alkenyl, —$(CH_2)_m$—R61, or R50 and R51, taken together with the N atom to which they are attached complete a heterocycle having from 4 to 8 atoms in the ring structure, one or more of which may be additional heteroatoms selected from N, O and S; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —$(CH_2)_m$—R61. Thus, the term "alkylamine" includes an amine group, as defined above, having a substituted or unsubstituted alkyl attached thereto, i.e., at least one of R50 and R51 is an alkyl group.

The term "acylamino" refers to a moiety that may be represented by the general formula:

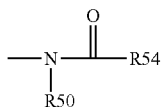

wherein R50 is as defined above, and R54 represents a hydrogen, an alkyl, an alkenyl or —$(CH_2)_m$—R61, where m and R61 are as defined above.

The term "amido" refers to an amino-substituted carbonyl and includes a moiety that may be represented by the general formula:

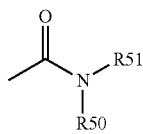

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—$(CH_2)_m$—R61, wherein m and R61 are defined above. Representative alkylthio groups include methylthio, ethyl thio, and the like.

The term "carboxyl" refers to such moieties as may be represented by the general formulas:

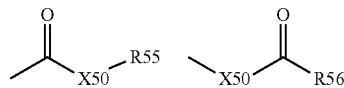

wherein X50 is a bond or represents an oxygen or a sulfur, and R55 and R56 represents a hydrogen, an alkyl, an alkenyl, —$(CH_2)_m$—R61 or a pharmaceutically acceptable salt, R56 represents a hydrogen, an alkyl, an alkenyl or —$(CH_2)_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The term "carbamoyl" refers to —O(C=O)NRR', where R and R' are independently H, aliphatic groups, aryl groups or heteroaryl groups.

The term "oxo" refers to a carbonyl oxygen (=O).

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—$(CH_2)_m$—R61, where m and R61 are described above.

The term "sulfonate" is art recognized and refers to a moiety that may be represented by the general formula:

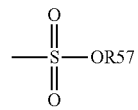

in which R57 is an electron pair, hydrogen, alkyl, cycloalkyl, or aryl.

The term "sulfate" is art recognized and includes a moiety that may be represented by the general formula:

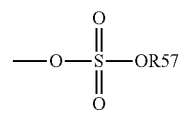

in which R57 is as defined above.

The term "sulfonamido" is art recognized and includes a moiety that may be represented by the general formula:

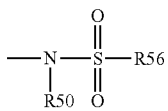

in which R50 and R56 are as defined above.

The term "sulfamoyl" is art-recognized and refers to a moiety that may be represented by the general formula:

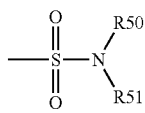

in which R50 and R51 are as defined above.

The term "sulfonyl" is art-recognized and refers to a moiety that may be represented by the general formula:

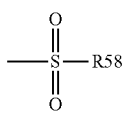

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

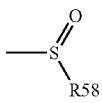

in which R58 is defined above.

The definition of each expression, e.g. alkyl, m, n, and the like, when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms (e.g., nitrogen) may have hydrogen substituents and/or any permissible substituents of organic compounds described herein which satisfy the valences of the heteroatoms.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The invention now being generally described, it will be more readily understood by reference to the following examples, which are included merely for purposes of illustration of certain aspects and embodiments of the present invention, and are not intended to limit the invention.

EXAMPLES

In experiments where the reduction products were UV active, the products were identified and the β/α ratio was determined using HPLC. General HPLC methods are as follows:

Column: Symmetry $C_{18}$ 5 um column, 4.6×150 mm
Solvent A: 0.1% aqueous trifluoroacetic acid
Solvent B: 0.1% trifluoroacetic acid in acetonitrile

| Method 1 | | |
|---|---|---|
| Time (min.) | % Solvent A | % Solvent B |
| 0.00 | 90.0 | 10.0 |
| 2.00 | 90.0 | 10.0 |
| 20.00 | 40.0 | 60.0 |
| 22.0 | 5.0 | 95.0 |
| 23.0 | 5.0 | 95.0 |
| 24.0 | 90.0 | 10.0 |
| 30.0 | 90.0 | 10.0 |

Signal: 215 nm

| Method 2 | | |
|---|---|---|
| Time (min.) | % Solvent A | % Solvent B |
| 0.00 | 70.0 | 30.0 |
| 2.00 | 70.0 | 30.0 |
| 12.0 | 5.0 | 95.0 |
| 13.0 | 5.0 | 95.0 |
| 13.10 | 70.0 | 30.0 |
| 15.0 | 70.0 | 30.0 |
| 0.00 | 70.0 | 30.0 |

Signal: 290 nm

Example 1

Reduction of Steroidal Enones

General Method:

The steroidal enone (100 mg) and 5% palladium on carbon (Johnson Matthey type A503023-5, 20 mg) were charged to a reaction vessel and 1 mL of solvent (3-picoline, pyridine or THF) was added. The reaction mixture was stirred and alternately degassed under vacuum and charged with hydrogen three times. The reaction mixture was stirred under balloon-pressure hydrogen until HPLC indicated the reaction was complete. The reaction mixture was filtered and the filtrate was analyzed by LCMS and HPLC. In those instances where the reduction products were UV active, the β/α ratio was determined by comparing the area under the HPLC curve for each product (retention times of each reaction product were compared against known standards). When the reduction products were not UV active (e.g., the reduced testosterone products), the β/α ratio was determined by integrating the LCMS peaks. The results are summarized in Table 1 below.

TABLE 1

| Steroid enone | β/α ratio in THF | β/α ratio in pyridine | β/α ratio in 3-picoline |
|---|---|---|---|
| Cyclopamine enone* | 5:1 | 10:1 | 24:1 |
| 4-Androstene-3,17-dione | 3:1 | 16:1 | 25:1 |
| Testosterone** | 13:1 | 100:1 | 100:1 |
| Cortisone | 0.7:1 | 4:1 | 8:1 |
| Progesterone | 3:1 | 29:1 | 48:1 |
| Adrenosterone | 0.8:1 | 1:1 | 1.2:1 |
| Prednisone | 1.7:1 | 1.9:1 | 1.2:1 |

*Cyclopamine enone has the following structure:

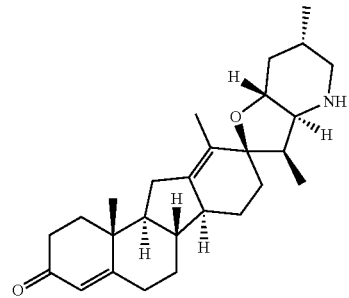

**The β/α ratio for the testosterone reduction products was determined by LCMS.

These results indicate that catalytic reduction of steroidal compounds using the 3-pyridine solvent 3-picoline generally increases the ratio of β/α reduction products. It is noted that the increase in selectivity was not shown for the reduction of prednisone. It was observed that the 1,2-ene of prednisone was reduced nearly twice as fast as the 4,5-ene:

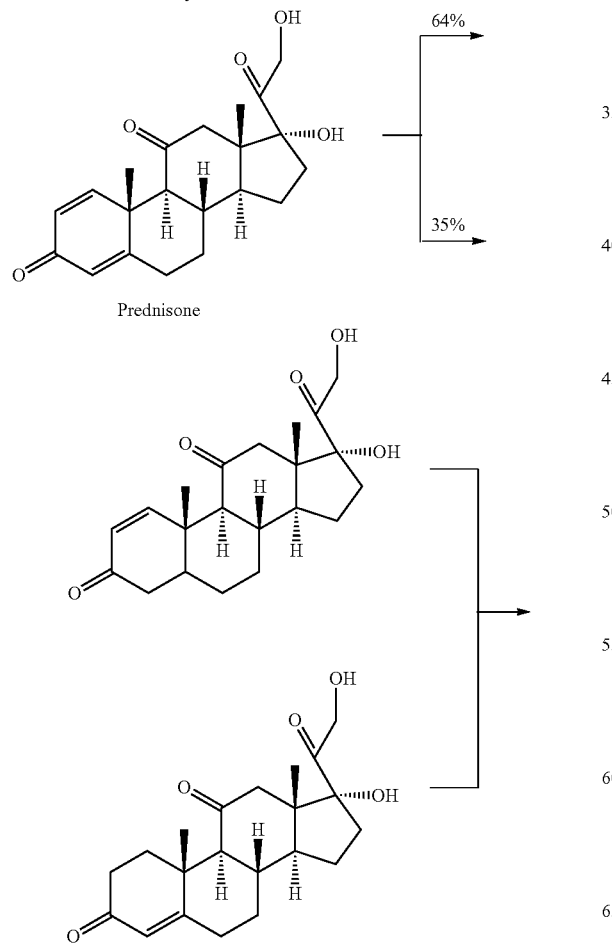

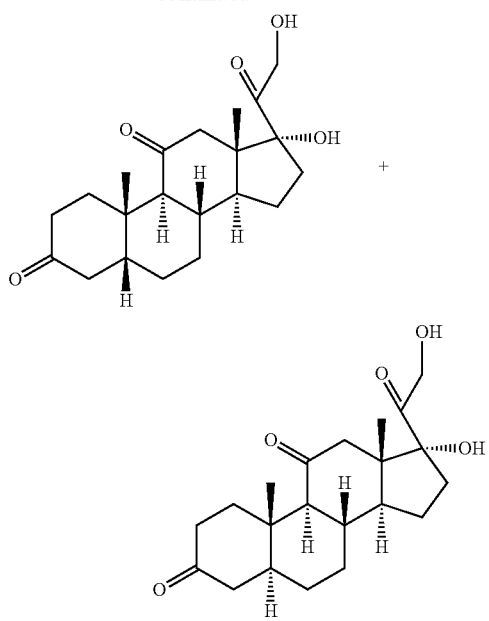

This difference in the rate of initial enone reduction may be responsible for the drop in β/α selectivity for the fully reduced products (and also the difference in selectivity between prednisone and cortisone).

Example 2

Solvents

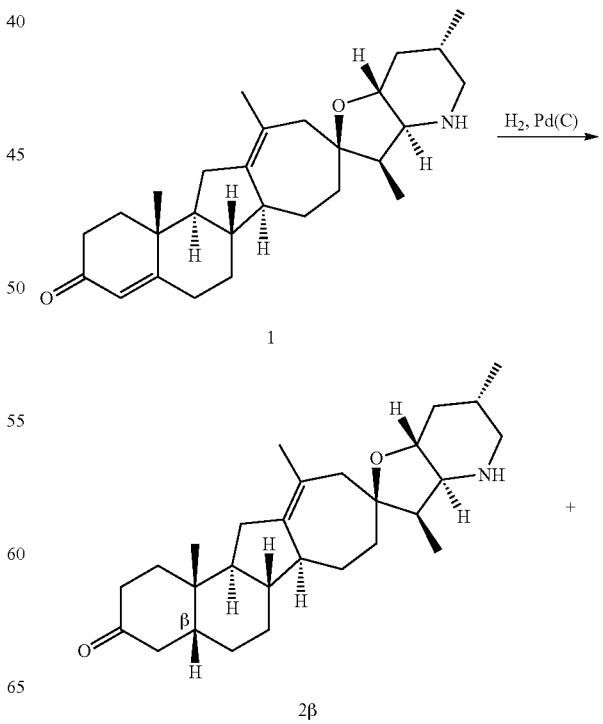

-continued

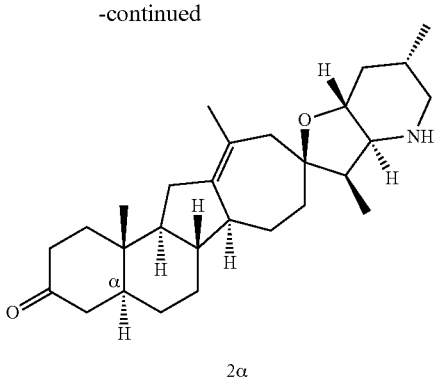

2α

General Method:

Compound 1 (~100 mg) and Degussa type E101 10% palladium on carbon (~20 mg) were charged to a reaction vessel and 1 mL of solvent was added. The reaction mixture was stirred and alternately degassed under vacuum and charged with hydrogen (balloon pressure) three times. The reaction mixture was stirred under balloon-pressure hydrogen until HPLC indicated the reaction was complete. The reaction mixture was filtered and the filtrate was analyzed by LCMS and HPLC. The β/α ratio was determined by comparing the area under the HPLC curve for each product (retention times of each reaction product were compared against known standards). The results are summarized in Table 2 below.

TABLE 2

| Solvent | β/α Product Ratio |
| --- | --- |
| Pyridine | 16:1 |
| 2,6-Lutidine | 9:1 |
| 2-Methoxypyridine | 11:1 |
| 3-Methoxypyridine | 54:1 |
| 4-Methoxypyridine | 32:1 |
| DMAP | 9:1 |
| 2-Picoline (2-methylpyridine) | 8:1 |
| 3-Picoline | 53:1 |
| 4-Picoline | 31:1 |
| 3-Acetoxypyridine | 27:1 |
| 3-isoButylpyridine | 15:1 |
| 3-Ethylpyridine | 40:1 |
| Ethyl-3-pyridylacetate | 24:1 |
| 3,5-Lutidine | 27:1 |
| 4-tertButylpyridine | 33:1 |

These results indicate that reducing the enone double bond of Compound 1 in 3-substituted pyridine solvents (e.g., 3-methoxypyridine, 3-picoline, 3-ethylpyridine) generally increases the β/α ratio of the reduction products, particularly compared to unsubstituted pyridine and 2-substituted pyridine solvents. The results also show that among isomeric pyridine solvents, (e.g., 2-, 3-, and 4-picoline and 2-, 3-, and 4-methoxypyridine) the 3-substituted pyridines provide the greatest selectivity for the β reduction product.

Example 3

Catalysts

Experiments were carried out as described in Example 2 above, using Compound 1 as substrate and 3-picoline as solvent. The results are summarized in Table 3 below.

TABLE 3

| Catalyst | β/α Product Ratio |
| --- | --- |
| 10% Degussa Pd/C | 53:1 |
| 5% Pd/C (JM type A401102-5) | 35:1 |
| 5% Pd/C (JM type A109047-5) | 35:1 |
| 5% Pd/C (JM type A405032-5) | 36:1 |
| 5% Pd/C (JM type A405038-5) | 32:1 |
| 5% Pd/C (JM type A503023-5) | 71:1 |
| 5% Pd/C (JM type A503032-5) | 49:1 |
| 5% Pd/C (JM type A503038-5) | 40:1 |
| 5% Pd/C (JM type A102023-5) | 63:1 |
| 5% Pd/C (JM type A102038-5) | 32:1 |
| 5% Pd/C (JM type A302011-5) | 24:1 |
| 5% Pd/C (JM type A302084-5) | 28:1 |
| 4% Pd, 1% Pt on carbon (JM type E101049-4/1) | 33:1 |

These results indicate that the increased β selectivity obtained by using the substituted pyridine solvent is maintained when a variety of hydrogenation catalysts are employed.

Example 4

Co-Solvents

Experiments were carried out as described in Example 2 above, using Compound 1 as substrate and various palladium catalysts in neat 3-picoline or a 10% solution (v/v) of 3-picoline in THF. The results are summarized in Table 4 below.

TABLE 4

| Catalyst | 3-Picoline β/α Product Ratio | 3-Picoline/THF β/α Product Ratio |
| --- | --- | --- |
| 10% Degussa Pd/C | 53:1 | 22:1 |
| 5% Pd/C (JM type A401102-5) | 35:1 | 14:1 |
| 5% Pd/C (JM type A109047-5) | 35:1 | 17:1 |
| 5% Pd/C (JM type A503023-5) | 71:1 | 15:1 |
| 5% Pd/C (JM type A503032-5) | 49:1 | 26:1 |
| 5% Pd/C (JM type A503038-5) | 40:1 | 16:1 |
| 5% Pd/C (JM type A102023-5) | 63:1 | 26:1 |
| 5% Pd/C (JM type A102038-5) | 32:1 | 20:1 |
| 5% Pd/C (JM type A302011-5) | 24:1 | 15:1 |
| 5% Pd/C (JM type A302084-5) | 28:1 | 16:1 |

Further experiments were carried out as described in Example 2 above, using Compound 1 as substrate and Degussa type E101 10% palladium on carbon or Pearlman's catalyst (palladium hydroxide on carbon) in neat 4-methoxypyridine (4-OMePy) or a 10% solution (v/v) of 4-methoxypyridine in a co-solvent. The results are summarized in Table 5 below.

TABLE 5

| Solvent | 10% Pd/C β/α ratio | Pearlman's cat. β/α ratio |
| --- | --- | --- |
| 4-OMePy | 32:1 | 27:1 |
| 10% 4-OMePy in THF | 20:1 | 18:1 |
| 10% 4-OMePy in EtOAc | 14:1 | 12:1 |
| 10% 4-OMePy in Toluene | 11:1 | 11:1 |
| 10% 4-OMePy in EtOH | 13:1 | 14:1 |

These results indicate that, while the use of neat substituted pyridine as solvent generally yields the highest β/α product ratio, the β reduction product continues to be favored when the substituted pyridine is used in conjunction with a co-solvent. In addition, these results indicate that the β reduction product continues to be favored when a variety of combinations of co-solvent and hydrogenation catalyst are employed.

Example 5

Co-Solvents

Experiments were carried out as described in Example 2 above, using Compound 1 as substrate and Degussa type E101 10% palladium on carbon as catalyst in neat 4-methoxypyridine (4-OMePy) or a 10% solution (v/v) of 4-methoxypyridine in a co-solvent. The results are summarized in Table 6 below.

TABLE 6

| Solvent | β/α Ratio |
| --- | --- |
| 4-OMePy | 32:1 |
| 10% 4-OMePy in THF | 20:1 |
| 10% 4-OMePy in Dioxane | 17:1 |
| 10% 4-OMePy in MTBE | 16:1 |
| 10% 4-OMePy in DME | 15:1 |
| 10% 4-OMePy in EtOAc | 14:1 |
| 10% 4-OMePy in Acetone | 13:1 |
| 10% 4-OMePy in EtOH | 13:1 |
| 10% 4-OMePy in Toluene | 11:1 |

These results indicate that, while the use of neat substituted pyridine as solvent generally yields the highest β/α product ratio, the β reduction product continues to be favored when the substituted pyridine is used in conjunction with a co-solvent.

Example 6

Side-Products

Side-product 2a was identified by HPLC and LCMS from the reduction of Compound 1 with Pd/C in the presence of pyridine:

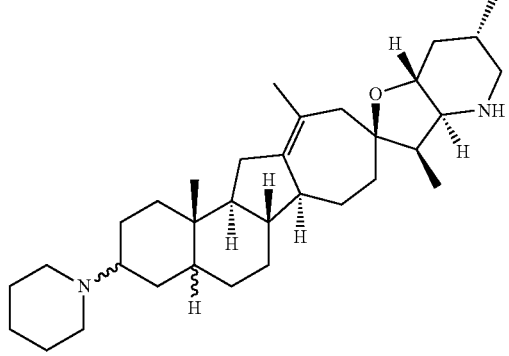

$C_{33}H_{54}N_2O$
Exact Mass: 494.42

Similarly, side-products 2b and 2c were identified from the reduction of Compound 1 with Pd/C in the presence of 4-methoxypyridine and 3-picoline, respectively:

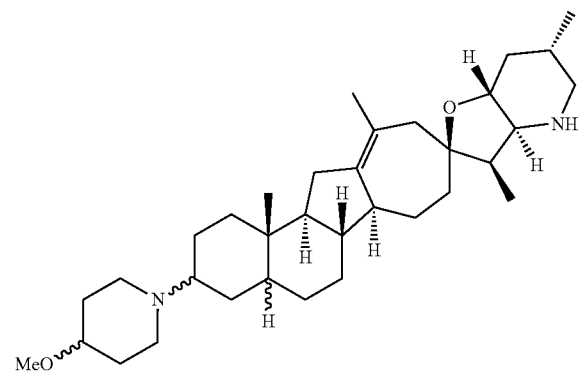

$C_{34}H_{56}N_2O_2$
Exact Mass: 524.43

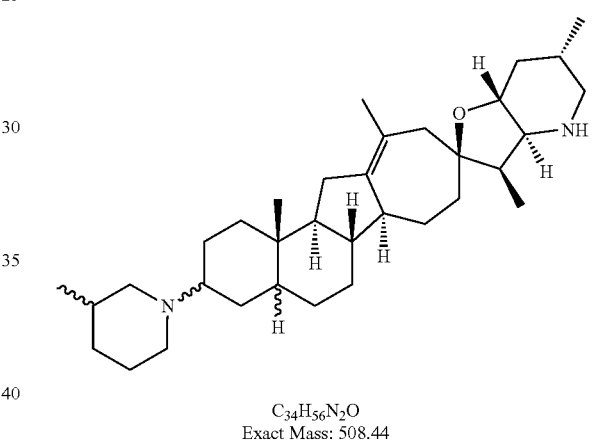

$C_{34}H_{56}N_2O$
Exact Mass: 508.44

In order to study side-product formation, experiments were carried out as described in Example 2 above, using Compound 1 as substrate and Degussa type E101 10% palladium on carbon as catalyst, while varying the solvent and extending the reaction time. The results are summarized in Table 7 below (percentages determined by HPLC).

TABLE 7

| Solvent | % Side-product at 17 h. | % Side-product at 65 h. |
| --- | --- | --- |
| 3-Picoline | 2 | 12 |
| 10% 3-Picoline in THF | 6 | 26 |
| 4-OMePy | 1 | 3 |
| Pyridine | 13 | 37 |

Example 7

Reduction of Compound 1

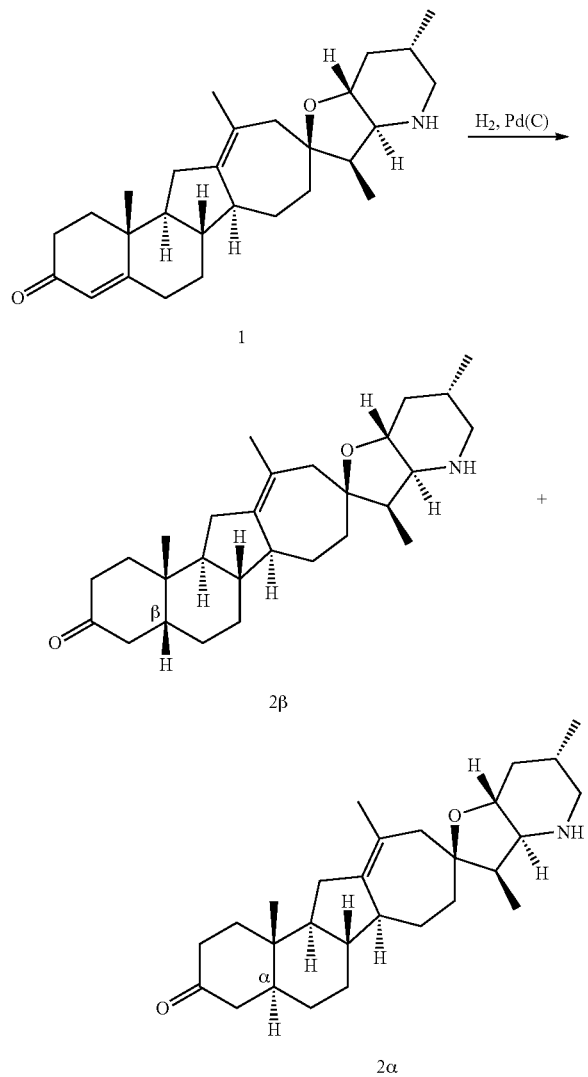

Compound 1 (459 mg) and Johnson-Matthey 5% palladium on carbon (A503023-5, 101 mg) were charged to an appropriately sized multi neck reaction vessel. The vessel was purged with nitrogen, then 3-picoline (2.2 g) was charged as the solvent. Stirring was started and the vessel was first degassed using nitrogen and then stirred under hydrogen at atmospheric pressure for 8 hours. At the end of the reaction, the catalyst was removed by filtration through 0.2 micron media, rinsing with ACN (1.4 ml). The filtrate and rinse were combined in a clean reaction vessel equipped with mechanical stirring, an internal temperature probe, and a nitrogen atmosphere.

A solution of citric acid (3.7 g) in water (9.2 ml) was charged to the reaction vessel at or below 30° C., and the reduced compound was allowed to slowly crystallize from solution as the citrate salt at 20° C. and then 0° C. The crystalline product was recovered by suction filtration and washed with water (3.7 ml). After drying, the citrate salt was isolated as a hydrate (3-5 wt % water) in 89.5% yield (622 mg) with a β/α ratio of 90:1. The citrate salt maintained its white color on storage at ambient temperature.

Example 8

Alternate Reduction of Compound 1

Compound 1 (20 g) was treated with balloon-pressure hydrogen gas in the presence of Johnson-Matthey 5% palladium on carbon (A503023-5, 4 g) in 3-picoline (200 mL), as described herein. When the reaction was judged complete after 7.5 hours, the catalyst was removed by filtration and the flask and filtration media were rinsed with THF (2×50 mL). The solution was concentrated to remove the THF, and 3N HCl (440 mL) at 5° C. was added. The filtrate-containing flask was rinsed with a solution of THF (20 mL) and water (20 mL) and the pH of the mixture was adjusted to 2.0 with 3N HCl. Water (200 mL) was added, and a white precipitate formed. The solid was transferred to a beaker and methyl t-butyl ether (400 mL) and saturated aqueous NaHCO3 (400 mL) were added. The organic layer was collected and filtered, and the aqueous layer was extracted with methyl t-butyl ether (2×100 mL). The combined organic layer was washed with water (2×200 mL), dried over anhydrous sodium sulfate and filtered. The filtrate was concentrated to yield the solid freebase product (17.42 g, 87%) with a β/α ratio of 76:1.

Example 9

Salt Formation

A. Synthesis of Reduced Product

Compound 1 (30.0 g) and Johnson-Matthey 5% palladium on carbon (A503023-5, 6.0 g) were charged to a 3000 mL round bottom flask, and 3-picoline (150 mL) was added. Stirring was started and the flask was degassed under vacuum and the charged with nitrogen three times. The flask was kept under balloon-pressure hydrogen atmosphere with stirring for 8 h. HPLC indicated that the reaction was not complete, so an additional 0.1 g of catalyst was added and the reaction was stirred under hydrogen for another 1.5 h. The catalyst was removed by filtration and the filtrate (164 g) was divided into portions for the salting study.

B. HCl Salt Formation

To 5.5 g of the filtrate was added acetonitrile (3.0 g). Hydrochloric acid (17 mL of 3N aqueous solution) was added. The pH of the solution was found to be 1.0. Water (10 g) was added and the mixture was stirred for 1.5 h. The solid precipitate was filtered (filtration time 2 min. 52 sec.) and dried to yield 0.95 g (87%) of a white solid. The salt turned slightly pink on storage at ambient temperature.

C. HBr Salt Formation

To 5.5 g of the filtrate was added acetonitrile (3.0 g). Hydrobromic acid (28 mL of 3N aqueous solution) was added. The pH of the solution was found to be 4.7. The mixture was stirred for 1.5 h. The solid precipitate was filtered (filtration time 1 min. 20 sec.) and dried to yield 0.97 g (82%) of a white solid. The salt turned light brown to black on storage at ambient temperature.

D. $H_2SO_4$ Salt Formation

To 5.5 g of the filtrate was added acetonitrile (3.0 g). Sulfuric acid (11 mL of 3N aqueous solution) was added. The pH of the solution was found to be 1.5. Water (16 g) and sodium chloride (1.0 g) were added and the mixture was stirred until a solid precipitate formed. The solid was filtered (filtration time 3 min. 23 sec.) and dried to yield 1.2 g (97%) of a white solid. The salt turned slightly pink on storage at ambient temperature.

E. Methanesulfonate Salt Formation

To 5.5 g of the filtrate was added acetonitrile (3.0 g). Methansulfonic acid (17 mL of 3N aqueous solution) was added. The pH of the solution was found to be 1.5. Water (10 g) and sodium bromide (1.73 g) were added and the mixture was stirred until a solid precipitate formed. The solid was filtered (filtration time 2 min. 35 sec.) and dried to yield 1.1 g (83%) of a white solid. The salt turned slightly pink on storage at ambient temperature.

The results of the various salt-producing experiments described in Examples 7 and 9 are summarized in Table 8 below.

TABLE 8

| Salt | % Yield | Appearance after storage |
|---|---|---|
| Citrate | 89.5 | White |
| HCl | 87 | Pink |
| HBr | 82 | Brown/black |
| $H_2SO_4$ | 97 | Pink |
| Methanesulfonate | 83 | Pink |

Example 10

Synthesis of Compound 42

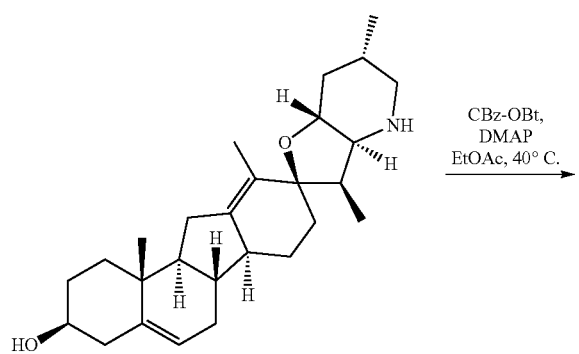

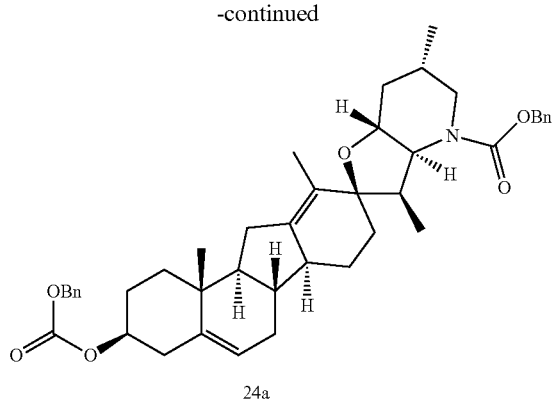

Recrystallized cyclopamine (2.07 g) was charged to an appropriately sized reaction vessel and placed under an inert atmosphere. EtOAc (7.6 g), triethylamine (1.53 g), and DMAP (307 mg) were added sequentially. The suspension was warmed to 40° C. Cbz-OBt was added in three portions over 90 minutes, keeping the internal temperature below 45° C. The reaction mixture was stirred at 40° C. for 90 minutes. The temperature was maintained while methanol (26.4 g) was slowly added to the reaction mixture. The resulting suspension was cooled to room temperature and stirred for at least 15 hours. The crude product was collected by filtration and rinsed with methanol (5 g). The white solid was dried under vacuum to a constant weight and recrystallized from heptane (30.3 g) and toluene (3.2 g) to afford Compound 24a (3.0 g).

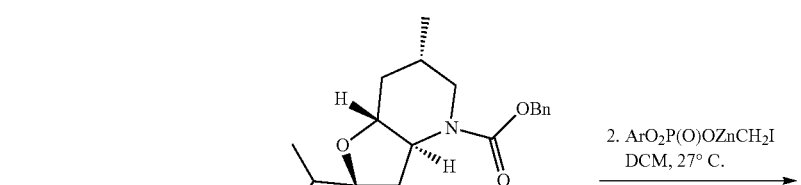

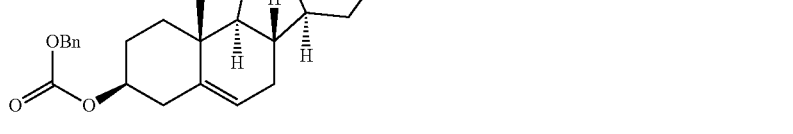

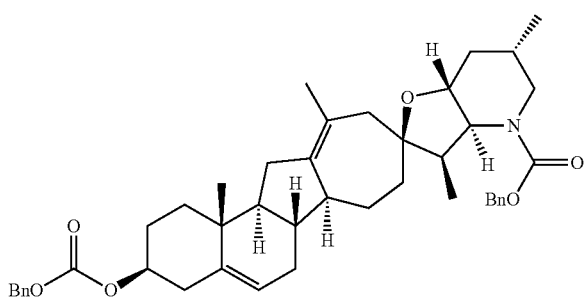

Solid bis(2,6-dimethylphenyl)hydrogenphosphate and 24a were pre-dried and placed under a nitrogen atmosphere. Neat diethyl zinc (722 mg) was charged to an appropriately sized reaction vessel containing DCM (9.0 g). DCM solutions of the phosphate (1.83 g in 17.9 g) and IPI-332690 (1.34 g in 3.6 g) were added sequentially at or below 25° C. Diiodomethane (1.58 g) was charged and the reaction was stirred at 28° C. for 4-6 hours. The reaction was cooled to −45° C. and a solution of methanesulfonic acid in DCM (566 mg in 1.5 g) was charged. After 15 minutes, morpholine (1.711 g) was added and the mixture was allowed to warm to room temperature overnight. The organic layer was washed twice with 2N HCl (2×13.6 g) then sequentially with 4.8 wt % sodium carbonate (aq), 4.8 wt % sodium sulfite (aq), and 4.8 wt % brine (13.6 g each). The organic layer was dried, filtered, concentrated to 4 g and diluted with isopropanol (4 g). The product was crystallized from solution by the slow addition of methanol (9.3 g). Filtration with a methanol rinse (2.6 g) and drying afforded 1.09 g of 24b (79% isolated yield).

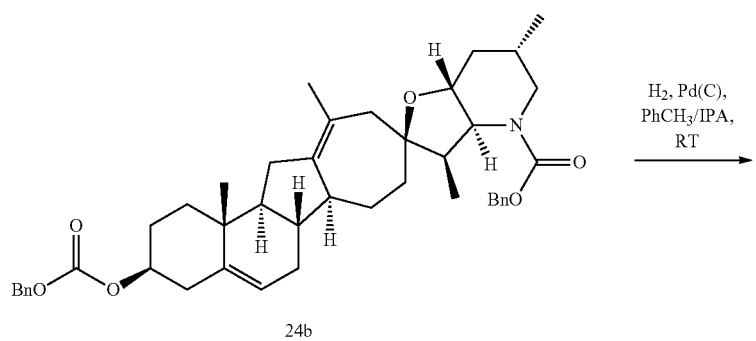

24b

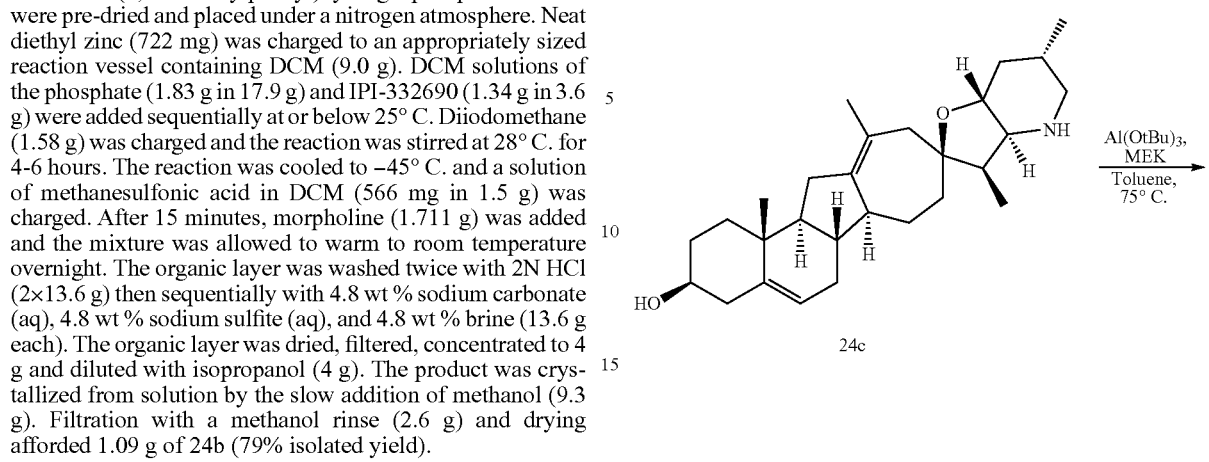

24c

Johnson Matthey Pd/C catalyst A-305038-5 (890 mg) was charged to an appropriately sized reaction vessel, followed by 24b (2.24 g). The reaction vessel was purged with N₂ and toluene (21.8 g) and 2-propanol (6.7 g) were added sequentially. The system was degassed and placed under a nitrogen atmosphere, and the process was repeated with hydrogen. The system was stirred vigorously and the hydrogen blanket was maintained at one atmosphere for 4-5 hours. Ethylenediamine (12.9 mg) was charged and the mixture was stirred for 15 minutes. The catalyst was removed by filtration with a toluene:IPA (3:1) rinse. The filtrate and rinses were concentrated and solvent exchanged to toluene. The product was crystallized from toluene (19.0 g) and heptane (18.0 g) to afford 24c as a white crystalline solid (1.34 g, 98% yield).

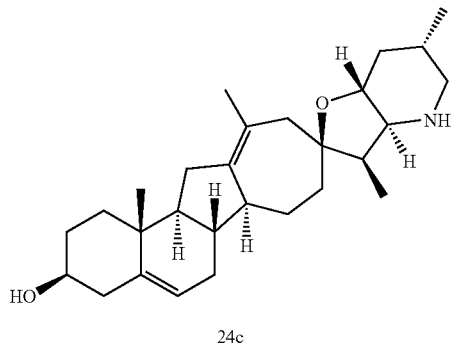

24c

-continued

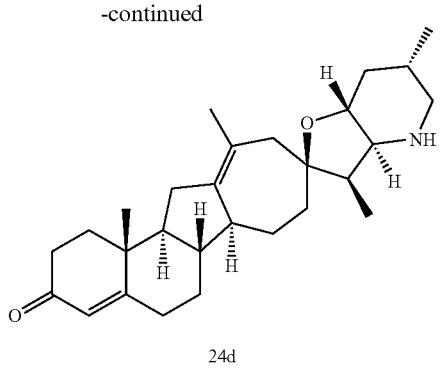

24d 24c (644 mg) was charged to an appropriately sized reaction vessel followed by aluminum t-butoxide (525 mg), toluene (8.34 g, 15 vol), and 2-butanone (7.83 g, 15 vol). The contents of the flask were degassed with evacuation/nitrogen purge cycles to remove oxygen and the reaction mixture was heated at 75° C. with vigorous stirring for 16-18 hours. The reaction was quenched by the addition of aqueous Rochelle's salt (2.6 g in 10.3 g water) and the mixture was vigorously stirred for one hour at 45° C. The aqueous and organic layers were separated. The aqueous layer was back extracted with a mixture of toluene (2.9 g) and EtOAc (2.9 g). The organic layers were combined and washed with fresh Rochelle's salt solution (2.6 g in 10.3 g water) and then with water (12.9 g). The resulting organic layer was dried over sodium sulfate (1.97 g), filtered, and concentrated in vacuo. The product was crystallized via a charge and concentration solvent exchange first to IPA (6.5 g) and then heptane (7.7 g). The thick heptane slurry (~2.7 g) was stirred overnight and solids were collected by filtration. Vacuum drying afforded 24d (550 mg) in an 85% yield.

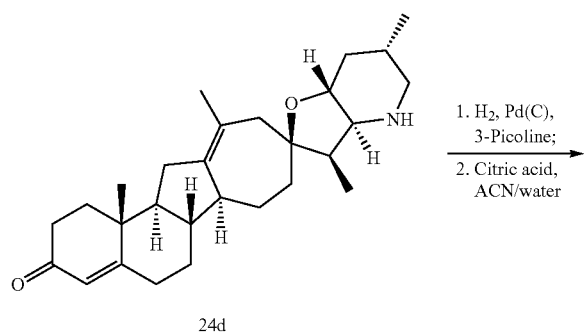

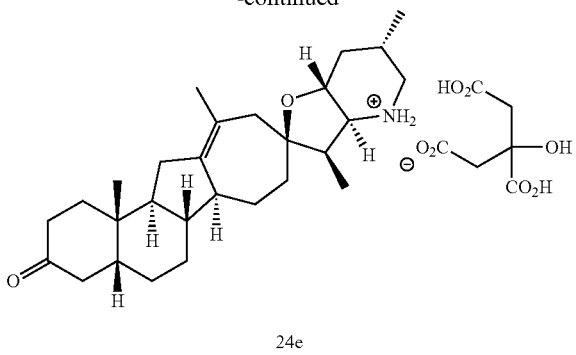

The enone 24d (459 mg) and Johnson-Matthey 5% palladium on carbon (A503023-5, 101 mg) were charged to an appropriately sized multi neck reaction vessel. The vessel was purged with nitrogen and 3-picoline (2.2 g) was charged as the solvent. Stirring was started and the vessel was first degassed using nitrogen and then stirred under hydrogen at atmospheric pressure for 8 hours. At the end of the reaction, the catalyst was removed by filtration through 0.2 micron media, rinsing with ACN (1.4 ml). The filtrate and rinse were combined in a clean reaction vessel equipped with mechanical stirring, an internal temperature probe, and a nitrogen atmosphere. A solution of citric acid (3.7 g) in water (9.2 ml) was charged to the reaction vessel at or below 30° C., and the product was allowed to slowly crystallize from solution as the citrate salt at 20° C. and then 0° C. The crystalline product was recovered by suction filtration and washed with water (3.7 ml). After drying, the citrate salt, 24e, was isolated as a hydrate (3-5 wt % water) in 89.5% yield (622 mg) with a β:α ratio approaching 90:1.

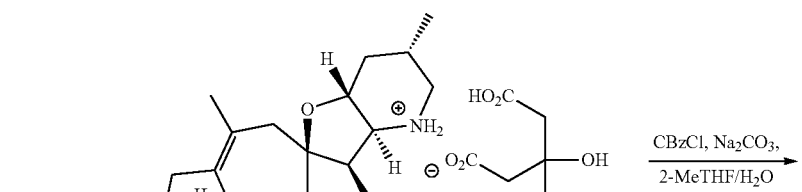

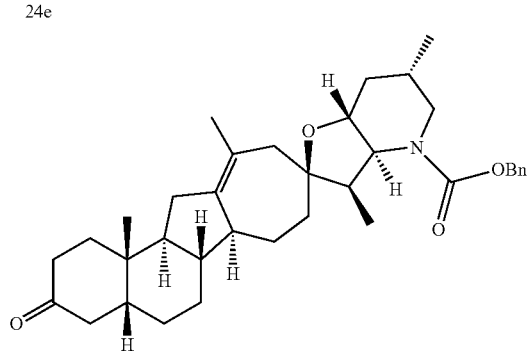

24e (1.50 g) was charged to the appropriately sized reactor along with 2-methyltetrahydrofuran (7.7 g) and 1M sodium carbonate (9.0 ml). A solution of benzyl chloroformate (454 mg) in 2-methyltetrahydrofuran (300 mg) was added via addition funnel and the reaction was stirred at ambient temperature for 1-2 hours. When the reaction was complete, the stirring was stopped, the layers were separated and the organic layer was washed twice with water (2×6 g). The organic layer was dried over sodium sulfate (3 g), filtered and concentrated. Residual water was reduced further by concentration from fresh 2-methyltetrahydrofuran (6.5 g) and the material was transferred as solution in anhydrous 2-methyltetrahydrofuran to the next reaction.

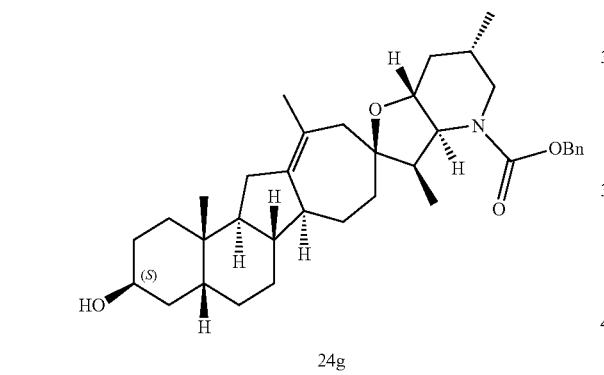

24f

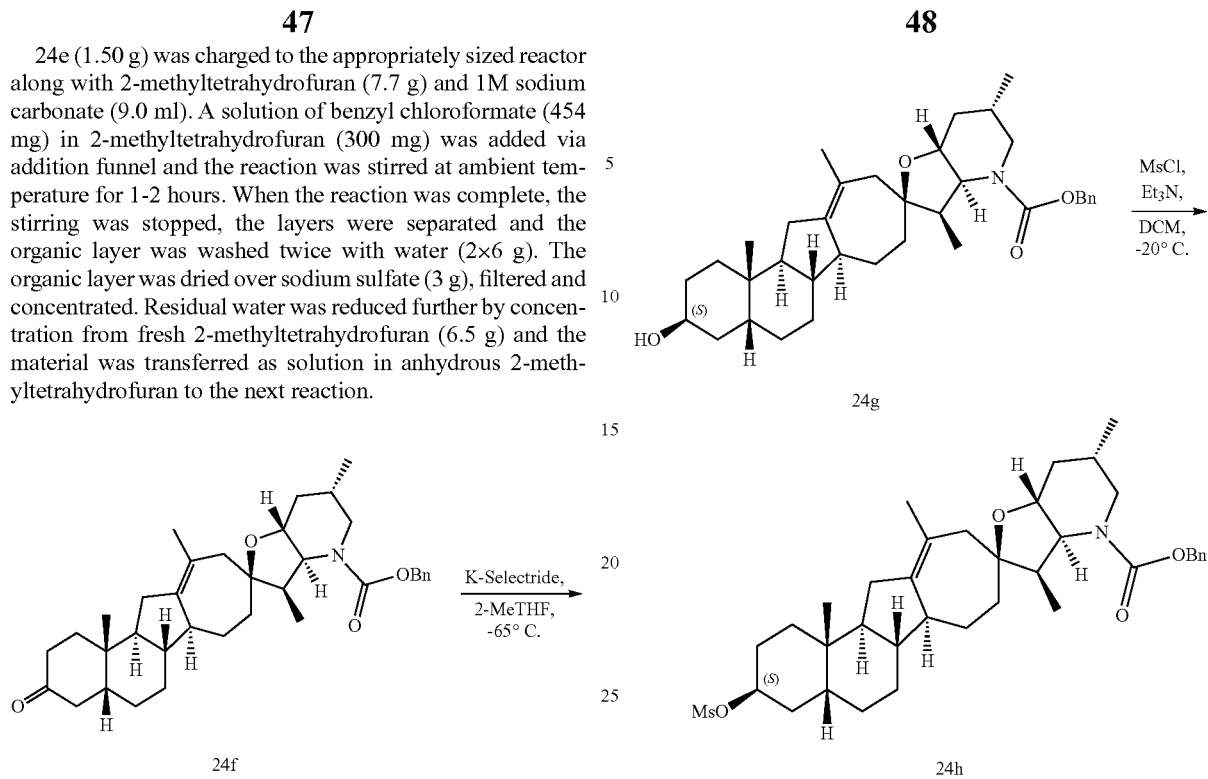

24g

Commercial 1 M K-Selectride® in THF (1.20 g) was charged to a dry reaction vessel under a nitrogen atmosphere, diluted with anhydrous 2-methyltetrahydrofuran (2.10 g) and cooled to −65° C. The solution of 24f (0.41 g) in 2-methyltetrahydrofuran (1.5 g) was then slowly added to the reaction vessel to control the internal temperature at −65±5° C. The reaction was stirred for 2 hours and warmed to −20° C. over approximately 1 hour and stirred for an additional hour. The reaction was quenched at low temperature with MeOH (0.33 g). The reagent was destroyed by the sequential addition of 3M NaOH (2.4 g) at −20° C. and 15% hydrogen peroxide in water (1.04 g) at or below 5° C., then the reaction was stirred overnight at ambient temperatures. The layers were separated and the organic layer was washed sequentially with 1M aqueous NaOH (2 ml), 0.5 M aqueous $Na_2SO_3$ (2 ml), and water (2 ml) adjusted to a pH of 3 with HCl. The organic layer was dried over sodium sulfate (0.82 g), filtered and concentrated. The product 24g (0.457 g) was re-concentrated from DCM (0.9 g) and used in the next reaction.

24g (1.36 g) was charged with anhydrous DCM (18.1 g) to an appropriately size reaction vessel, place under an inert atmosphere and cooled to −20° C. Triethylamine (0.61 mg) was charged followed by the slow addition of methanesulfonyl chloride (373 mg) in anhydrous DCM (300 mg). The reaction was stirred for 1 hour at −20° C. When complete, the reaction was quenched with water (13.6 g) and allowed to warm. The layers were separated and the organic layer was washed with 2.5 wt % sodium bicarbonate (13.8 g) and then water (10.9 g). The organic layer was dried over sodium sulfate (4 g), filtered, and concentrated. The product solution was solvent exchanged via charge and concentration to t-butyl methyl ether (10.9 ml) and then 1,3-dimethyl-3,4,5,6-tetrahydro-2(1H)-pyrimidinone (DMPU, 4.7 ml). The DMPU solution was used directly in the next reaction.

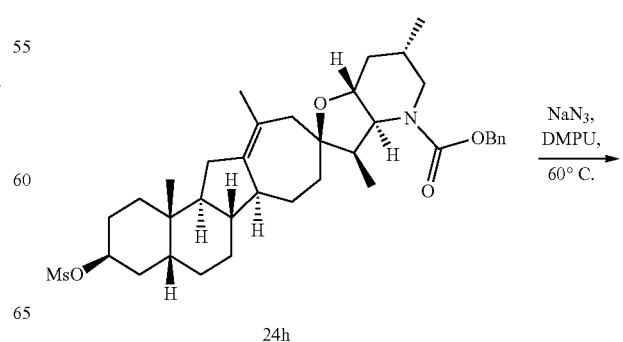

24h

-continued

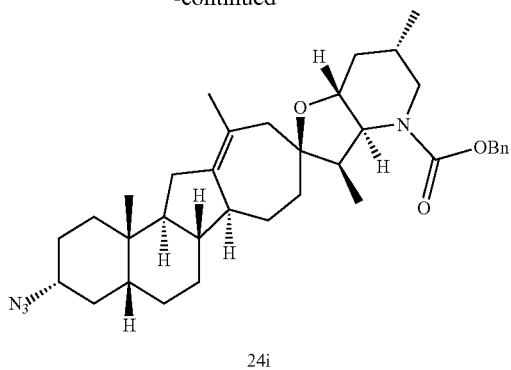

24i

Sodium azide (0.74 g) was charged to an appropriately sized reaction vessel. The solution of 24h (1.46 g) in DMPU (5.9 g) was charged to the reaction vessel, rinsing with additional DMPU (1.9 g). The suspension was heated to 60° C. for 15 hours, maintaining a nitrogen sweep for the entire reaction. The reaction was cooled to ambient temperature and diluted with MTBE (11.7 g). The organic solution was washed 3 times with 2% saline (3×8 g), dried over sodium sulfate (4.4 g), filtered, and concentrated. The product was concentrated from THF (6.4 g) and used directly in the next reaction.

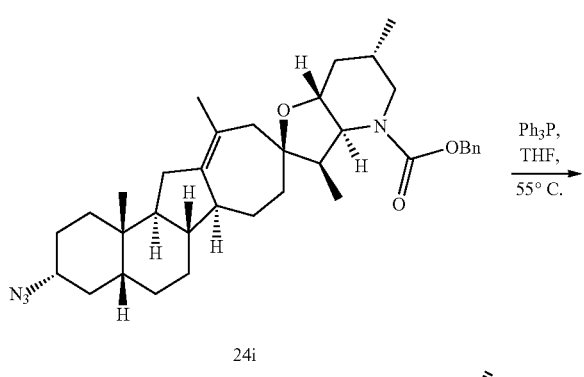

24i

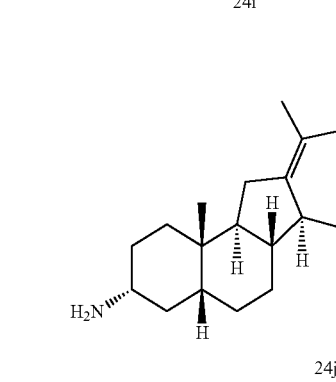

24j

The crude 24i (1.34 g) was dissolved and transferred to a suitably sized reaction vessel with THF (12.6 g). Triphenylphosphine (0.70 g) and water (0.44 g) were charged and the reaction is heated to 55° C. for 15-24 hours. When complete, the reaction was cooled to ambient temperature, dried with magnesium sulfate (1.4 g), filtered and concentrated.

The solids were dissolved and concentrated from three portions of DCM (3×9 g) and purified by silica gel chromatography using DCM/MeOH/Et$_3$N gradients to remove reagent based impurities. The pooled fractions were concentrated to dryness, dissolved in DCM (6.8 g) and concentrated to dryness again to afford an amorphous solid (1.12 g) which was used in the next reaction.

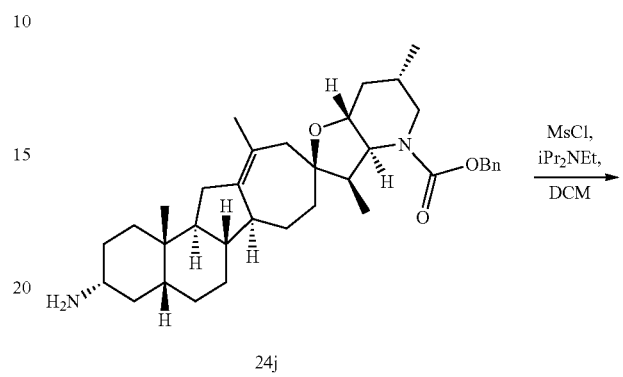

24j

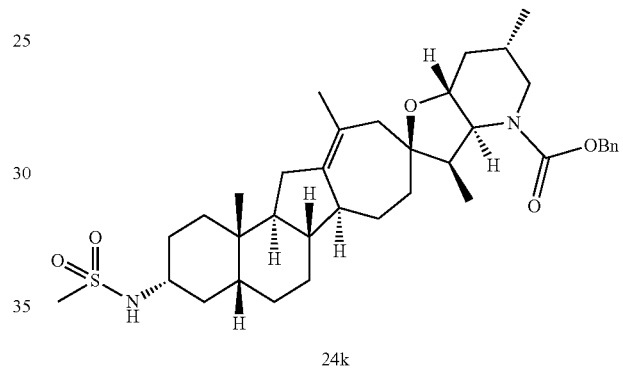

24k 24j (1.09 g) was dissolved and transferred to an appropriately sized reaction vessel with anhydrous DCM (15.8 g) and placed under a nitrogen atmosphere. The solution was cooled to 0° C. Diisopropylethylamine (357 mg) and neat methanesulfonyl chloride (0.165 ml) were charged sequentially while maintaining temperature between below 5° C. The reaction was quenched with 0.4 M aqueous sodium bicarbonate (11.4 g) and warmed to ambient temperature. The layers were separated and the aqueous phase was back extracted with DCM (5.8 g). The combined organic layers were dried over magnesium sulfate (0.55 g), filtered and concentrated. The product 24k was dissolved and striped from 2-propanol (4.0 g) to remove residual DCM and used directly in the next reaction.

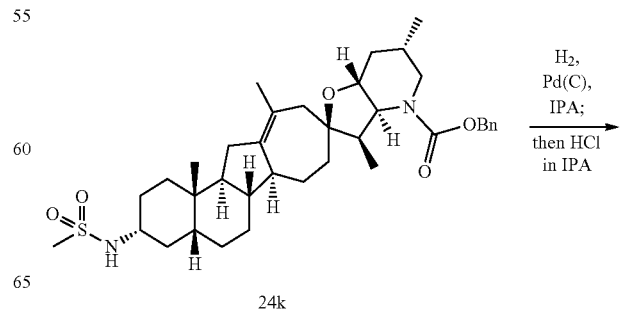

24k

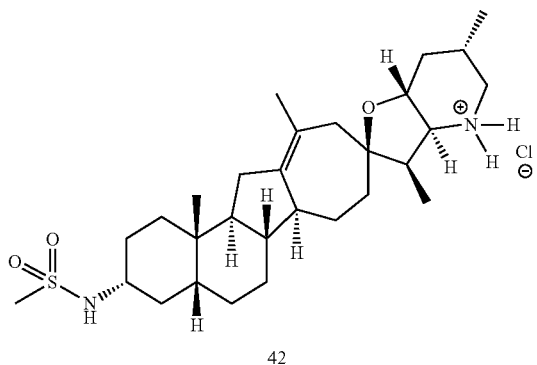

Aldrich Degussa type E101 NE/W 10% Pd/C (249 mg) was charged to an appropriately sized reaction vessel and placed under a nitrogen atmosphere. A 2-propanol (9.8 g) solution of 24k (1.24 g) was charged to the reaction vessel. The system was degassed and placed under a nitrogen atmosphere, and the process was repeated with hydrogen. The reaction was stirred under 1 atm of hydrogen at ambient temperature for 8 hours. An inert atmosphere was returned to the vessel and a second charge of catalyst (125 mg) slurried in 2-propanol (0.5 g) was added to the reaction. The reaction mixture was degassed and placed under a nitrogen atmosphere, and the process was repeated with hydrogen. The reaction was stirred under 1 atm of hydrogen for another 15 hours at ambient temperature. When complete, the reaction was filtered, treated with steam activated carbon (200 mg), and filtered again. The solution was dried by partial concentration transferred to a reaction vessel and diluted with anhydrous 2-propanol to 0.09 M based on the theoretical yield. A 1.25 M HCl solution in 2-propanol (1.64 g) was charged over 20 minutes. The hydrochloride salt crystallizes slowly with gentle stirring and was isolated by filtration. The crystals were washed with 2-propanol (2.5 g) and vacuum dried to afford Compound 42 (916 mg, 80% yield) as a 1:1 IPA solvate.

Those skilled in the art will recognize, or be able to ascertain using no more than routine experimentation, many equivalents to the specific embodiments of the invention described herein. Such equivalents are intended to be encompassed by the following claims.

What is claimed is:

1. A method of making a mixture of a compound having formula V and a compound having formula VI:

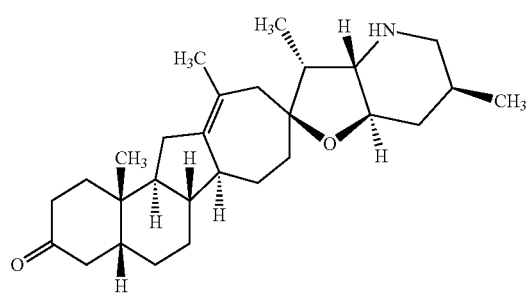

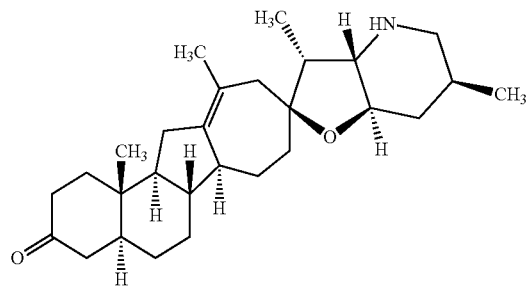

the method comprising treating a compound having formula VII:

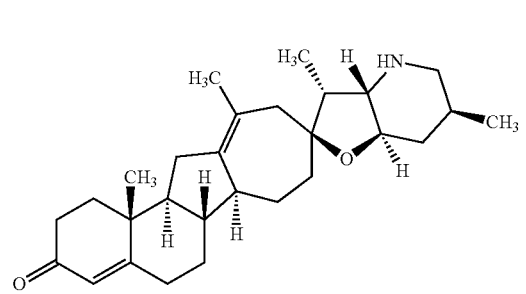

in a solvent with hydrogen gas in the presence of a palladium on carbon catalyst and a substituted pyridine, wherein the ratio of the β ketone product V to the α ketone product VI is at least 3:1.

2. The method of claim 1, wherein the ratio of the compound of formula V to compound of formula VI is at least 10:1, or the ratio of the compound of formula V to compound of formula VI is at least 20:1, or the ratio of the compound of formula V to compound of formula VI is at least 30:1, or the ratio of the compound of formula V to compound of formula VI is at least 40:1.

3. The method of claim 1, wherein the substituted pyridine is a 3-substituted pyridine.

4. The method of claim 3, wherein the 3-substituted pyridine is 3-picoline.

5. The method of claim 1, wherein the substituted pyridine is a 4-substituted pyridine.

6. The method of claim 5, wherein the 4-substituted pyridine is selected from 4-picoline and 4-methoxypyridine.

7. The method of claim 1, wherein the solvent comprises the substituted pyridine.

8. The method of claim 7, wherein the solvent comprises 3-picoline.

9. The method of claim 1, further comprising adding an aqueous solution of citric acid and isolating the salt of compounds V and VI.

10. The method of claim 9 further comprising making a compound of formula XV:

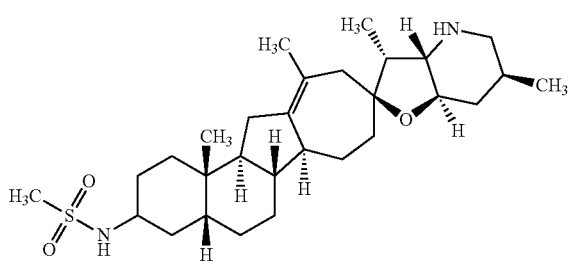

XV the method further comprising the steps of:
(a) treating a compound of formula IX:

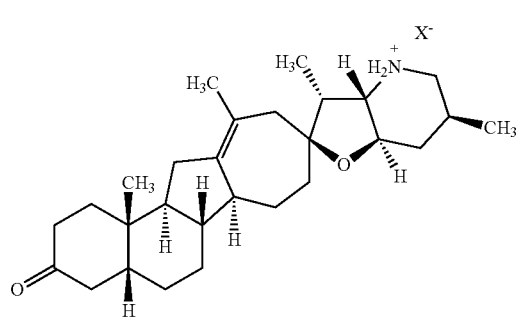

IX wherein X⁻ is citrate, CBzCl to produce a compound of formula XI:

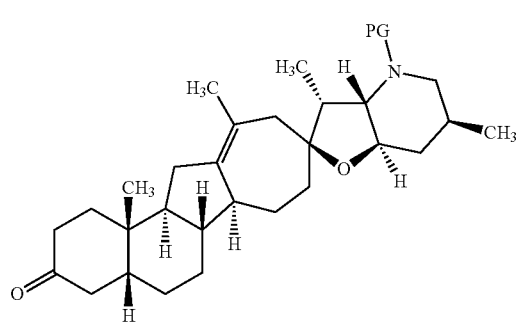

XI wherein PG is CBz;
(b) treating the compound of formula XI with a K-Selectride to produce an alcohol of formula XII:

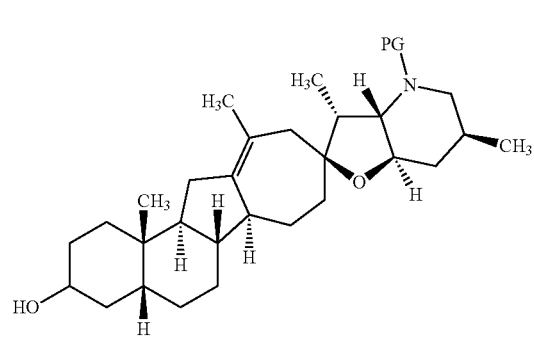

XII (c) converting the alcohol of formula XII to an amine of formula XIII:

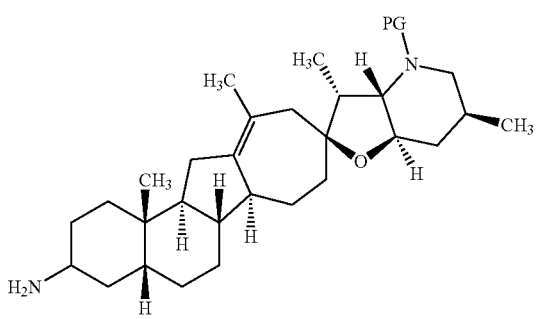

XIII (d) treating the amine of formula XIII with mewl chloride to produce a sulfonamide of formula XIV:

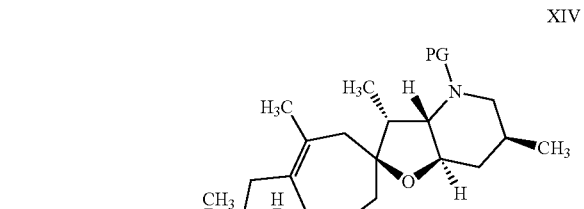

XIV and
(e) deprotecting the sulfonamide of formula XIV to produce the compound of formula XV.

11. The method of claim 10, wherein step (c) comprises:
(1) converting the alcohol to a mesylate leaving group to produce a compound of formula XVI:

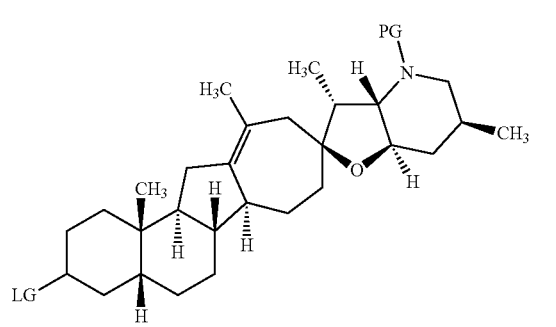

XVI wherein LG is mesylate;
(2) treating the compound of formula XVI with sodium azide to produce a compound of formula XVII:

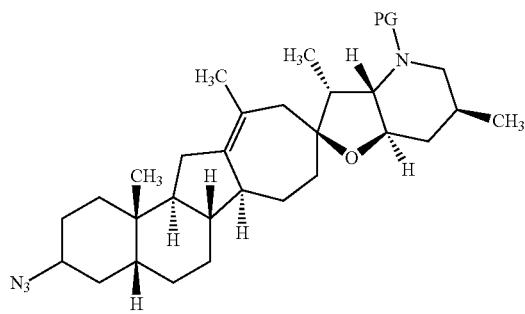

XVII and
(3) treating the compound of formula XVII with triphenylphosphine to form the amine of formula XIII.

12. The method of claim 10, wherein the sulfonamide of formula XIV is deprotected by treatment with hydrogen gas in the presence of a catalyst to form the compound of formula XV.

13. The method of claim 10, wherein the compound of formula XV has the following absolute stereochemistry:

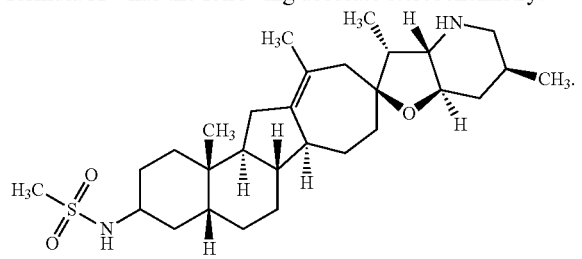

14. The method of claim 10, further comprising the step of treating the compound of formula XV with HCl to produce a compound of formula XIX:

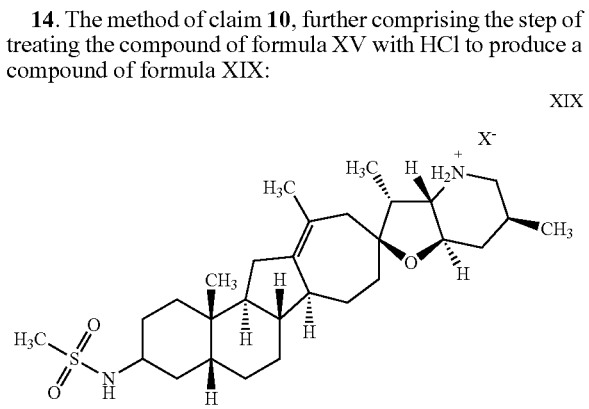

XIX wherein X⁻ is chloride.

15. A mixture comprising a compound of formula V, or a pharmaceutically acceptable salt thereof:

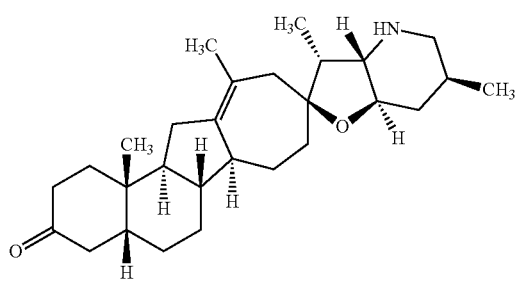

V and a compound of formula 2c, or a pharmaceutically acceptable salt thereof:

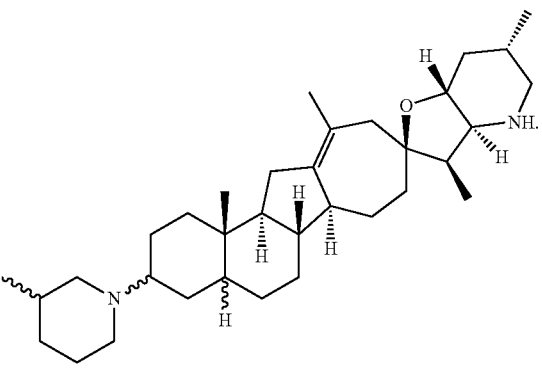

2c

16. The mixture of claim 15, wherein the compound of formula 2c is present in less than 1%.

* * * * *